US009839617B2

(12) United States Patent
Benita et al.

(10) Patent No.: US 9,839,617 B2
(45) Date of Patent: Dec. 12, 2017

(54) NANOENCAPSULATION OF HYDROPHILIC ACTIVE COMPOUNDS

(71) Applicant: Yissum Research Development Company of the Hebrew University of Jerusalem Ltd., Jerusalem (IL)

(72) Inventors: Simon Benita, Tel Aviv (IL); Taher Nassar, Kfar Tur'an (IL); Liat Kochavi-Soudry, Shoham (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/114,212

(22) PCT Filed: Jan. 26, 2015

(86) PCT No.: PCT/IL2015/050091
§ 371 (c)(1),
(2) Date: Jul. 26, 2016

(87) PCT Pub. No.: WO2015/111062
PCT Pub. Date: Jul. 30, 2015

(65) Prior Publication Data
US 2016/0361267 A1  Dec. 15, 2016

Related U.S. Application Data

(60) Provisional application No. 61/931,910, filed on Jan. 27, 2014, provisional application No. 62/080,607, filed on Nov. 17, 2014.

(51) Int. Cl.
| A61K 9/51 | (2006.01) |
|---|---|
| A61K 9/14 | (2006.01) |
| A61K 38/28 | (2006.01) |
| A61K 38/26 | (2006.01) |
| A61K 9/00 | (2006.01) |
| A61K 9/16 | (2006.01) |
| A61K 38/25 | (2006.01) |
| A61K 38/38 | (2006.01) |
| A61K 31/404 | (2006.01) |
| A61K 38/22 | (2006.01) |
| A61K 47/48 | (2006.01) |

(52) U.S. Cl.
CPC .......... *A61K 9/5161* (2013.01); *A61K 9/0053* (2013.01); *A61K 9/146* (2013.01); *A61K 9/1635* (2013.01); *A61K 9/1652* (2013.01); *A61K 9/5153* (2013.01); *A61K 9/5169* (2013.01); *A61K 9/5192* (2013.01); *A61K 31/404* (2013.01); *A61K 38/2278* (2013.01); *A61K 38/25* (2013.01); *A61K 38/26* (2013.01); *A61K 38/28* (2013.01); *A61K 38/385* (2013.01); *A61K 47/482* (2013.01); *A61K 47/48215* (2013.01); *A61K 47/48915* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| 3,654,083 A | 4/1972 | Moelker |
| 3,896,092 A | 7/1975 | Epton et al. |
| 4,970,156 A | 11/1990 | Avrameas et al. |
| 2001/0051189 A1* | 12/2001 | Alonso Fernandez ........... A61K 9/5161 424/499 |
| 2002/0169120 A1* | 11/2002 | Blanchat ................. A61L 27/20 424/423 |
| 2010/0021549 A1* | 1/2010 | Meyrueix ................ A61K 8/11 514/1.1 |
| 2011/0008450 A1* | 1/2011 | Moore ................... A61K 9/145 424/490 |

FOREIGN PATENT DOCUMENTS

| ES | 2 382 625 A1 | 6/2012 | |
| JP | 58-76089 A | 5/1983 | |
| WO | 88/09163 A1 | 12/1988 | |
| WO | 89/03207 A1 | 4/1989 | |
| WO | 91/06282 A1 | 5/1991 | |
| WO | 95/13798 A1 | 5/1995 | |
| WO | WO 9513798 A1 * | 5/1995 | .......... A61K 9/1652 |
| WO | 95/34328 A1 | 12/1995 | |
| WO | 2012/101639 A2 | 8/2012 | |
| WO | WO 2013042125 A2 * | 3/2013 | .......... A61K 9/0019 |

OTHER PUBLICATIONS

KB Chalasani, GJ Russell-Jones, AK Jain, PV Diwan, SK Jain. "Effective oral delivery of insulin in animal models using vitamin B12-coated dextran nanoparticles." Journal of Controlled Release, vol. 122, 2007, pp. 141-150.*
CB Woitiski, RJ Neufeld, F Veiga, RA Carvalho, IV Figueiredo. "Pharmacological effect of orally delivered insulin facilitated by multilayered stable nanoparticles." European Journal of Pharmaceutical Sciences, vol. 41, 2010, pp. 556-563.*
AO Elzoghby, WM Samy, NA Elgindy. "Albumin-based nanoparticles as potential controlled release drug delivery systems." Journal of Controlled Release, vol. 157, 2012, pp. 168-182.*
D Jain, AK Panda, DK Majumdar. "Eudragit S100 Entrapped Insulin Microspheres for Oral Delivery." AAPS PharmSciTech, vol. 6(1), 2005, Article 16, pp. E100-E107.*
CP Reis, FJ Veiga, AJ Ribeiro, RJ Neufeld, C Damge. "Nanoparticulate Biopolymers Deliver Insulin Orally Eliciting Pharmacological Response." Journal of Pharmaceutical Sciences, vol. 97, No. 12, Dec. 2008, pp. 5290-5305.*
Gursoy et al., "Self-emulsifying drug delivery systems (SEDDS) for improved oral delivery of lipophilic drugs", Biomedicine & Pharmacotherapy, vol. 58, pp. 173-182, (2004).
Joshi et al., "Lipid nanoparticles for parenteral delivery of actives", European Journal of Pharmaceutics and Biopharmaceutics, vol. 71, pp. 161-172, (2009).
Kluge et al., "Rational design of drug-polymer co-formulations by CO2 anti-solvent precipitation", J. of Supercritical Fluids, vol. 48, pp. 176-182, (2009).

(Continued)

*Primary Examiner* — Isaac Shomer
(74) *Attorney, Agent, or Firm* — Vorys, Sater, Seymour and Pease LLP

(57) ABSTRACT

Provided is a nanoparticle including a water-soluble protein, a glucan and a hydrophilic active agent, the glucan being at least partially cross-linked by a metaphosphate.

19 Claims, 15 Drawing Sheets

(56) References Cited

OTHER PUBLICATIONS

Mehnert et al., "Solid lipid nanoparticles Production, characterization and applications", Advanced Drug Delivery Reviews, vol. 47, pp. 165-196, (2001).
Mundargi et al., "Nano/micro technologies for delivering macromolecular therapeutics using poly(D,L-lactide-co-glycolide) and its derivatives", Journal of Controlled Release, vol. 125, pp. 193-209, (2008).
Reichert, "Trends in US approvals: new biopharmaceuticals and vaccines", Trends in Biotechnology, vol. 24, No. 7, pp. 293-298, (2006).
Woitiski et al., "Design for optimization of nanoparticles integrating biomaterials for orally dosed insulin", European Journal of Pharmaceutics and Biopharmaceutics, vol. 73, pp. 25-33, (2009).
Zorzi et al., "Hybrid Nanoparticle Design Based on Cationized Gelatin and the Polyanions Dextran Sulfate and Chondroitin Sulfate for Ocular Gene Therapy", Macromol. Biosci., vol. 11, pp. 905-913, (2011).
Almeida et al., "Solid lipid nanoparticles as a drug delivery system for peptides and proteins", Advanced Drug Reviews, vol. 59, pp. 478-490, (2007).
Bilati et al, "Strategic approaches for overcoming peptide and protein instability within biodegradable nano- and microparticles", European Journal of Pharmaceutics and Biopharmaceutics, vol. 59, pp. 375-388, (2005).
Tsuji et al., "Approval of new biopharmaceuticals 1999-2006: Comparison of the US, EU and Japan situations", European Journal of Pharmaceutics and Biopharmaceutics, vol. 68, pp. 496-502, (2008).

\* cited by examiner

NANOENCAPSULATION OF HYDROPHILIC ACTIVE COMPOUNDS

TECHNOLOGICAL FIELD

The invention generally concerns nanoparticles comprising hydrophilic active compounds and nanoencapsulation processes for their preparation.

BACKGROUND OF THE INVENTION

The majority of peptide and protein drugs are still administered by daily injections, thus being associated with compliance problems, pain-associated problems and major inconveniences to the patients. Hence, either prolonged injectable delivery systems or non-invasive delivery systems for such drugs are required.

The oral route offers the advantage of self-administration with high patient acceptance and compliance.

Oral and injectable prolonged release delivery of peptides and proteins remains challenging and continues to be the most attractive alternatives to the parenteral conventional delivery requiring daily administration. Despite intensive efforts invested over the last two decades no viable solution for oral delivery of hydrophilic potent macromolecules has emerged because of several drawbacks and hurdles associated with the poor intestinal membrane permeability of these hydrophilic macromolecules, limited oral bioavailability, instability in the gut and extensive rapid metabolism.

For the purpose of developing oral protein delivery systems with marked bioavailability, three approaches may be adopted:

(a) modification of the physicochemical properties of macromolecules;

(b) new functionalization of macromolecules; or (c) use of improved cargo delivery via nanocarriers.

Nevertheless, it is essential, irrespective of the approach to maintain the initial biological activity of the proteins. An oral delivery system will need to enhance the intestinal membrane permeability of such macromolecules significantly to have a chance to be considered of potential for further clinical testing. A number of nano- and microparticulate delivery systems have been used to improve the oral absorption of the hydrophilic macromolecules and exhibited promising results, but are still suffering from limitations in term of intestinal absorption and drug stability protection.

Nano-sized systems (e.g., liposomes, lipid and polymeric nanoparticles, micelles, etc.) have been found to be advantageous over traditional formulations for protein delivery. Biotech drugs are predicted to become the main source of therapeutics in the near future [1]. Nevertheless, the therapeutic exploitation of such molecules relies on the possibility to develop suitable formulations that can satisfactorily overcome the intrinsic limitations of their use; namely low oral bioavailability and biological and physicochemical instability. However, oral administration of protein drugs encountered many difficulties due to their proteolytic instabilities and limited abilities to traverse biological barriers. Liposomes and micelles based delivery systems are not stable in the gut lumen and cannot elicit the adequate protection to the sensitive macromolecules.

Therefore, among the pharmaceutical formulations, nanoparticles have been successfully explored for drug delivery of peptidic drugs [2-4]. Nanoparticles, more specifically the biodegradable polymeric nanoparticles, possess excellent tissue biocompatibility, biodegradability, composition flexibility and small size, making them suitable for a variety of applications. Furthermore, these formulations were shown to enhance the drug bioavailability following oral administration [5].

Although encapsulation with biodegradable polymers is very attractive, the manufacturing processes are still complicated and expensive for hydrophilic macromolecules. In case of efficient entrapment approaches of protein drugs into these systems, encapsulation using polymers may provide (a) protection to the proteins from degradation during storage and delivery and (b) a sustained release profile when desired [6-8].

REFERENCES

[1] Tsuji, K., Tsutani, K. *Eur. J. Pharm. Biopharm.*, 2008, 68, 496-502

[2] Joshi, M. D., Muller, R. H. *Eur. J. Pharm. Biopharm.*, 2009, 71, 161-172

[3] Kluge, J., Fusaro, F., Muhrer, G., Thakur, R., Mazzotti, M., *J. Supercrit. Fluids*, 2009, 48, 176-182

[4] Mehnert, W., Mader, K. *Adv. Drug Deliv. Rev.*, 2001, 47, 165-196

[5] Gursoy R N, Benita S., *Biomed Pharmacother.*, 2004, 58, 173-82

[6] Almeida, A. J., Souto, E. *Adv. Drug Deliv. Rev.*, 2007, 59, 478-490

[7] Bilati, U., Allémann, E., Doelker, E. *Eur. J. Pharm. Biopharm.*, 2005, 59, 375-388

[8] Mundargi, R. C., Babu, V. R., Rangaswamy, V., Patel, P., Aminabhavi, T. M. *J. Control. Release*, 2008, 125, 193-209

[9] WO 2012/101639

SUMMARY OF THE INVENTION

The present invention provides nanoencapsulation of hydrophilic bio-macromolecules for protecting and controlling peptidic drug release. This novel strategy allows the controlled release of small peptidic drug species loaded within nanoparticles, rather than the release of dissolved drug in the vicinity of the mucosa when microencapsulated within a blend of polymeric or alternatively following parenteral administration when double nanoencapsulated using nano-spray drying technology already described [9]. Such encapsulation provides protection of sensitive macromolecules from acidic environment in case of oral administration, and also from degradation by proteolytic enzymes irrespectively of the route of administration.

Thus, in one of its aspects, the invention provides a nanoparticle comprising a water-soluble protein, a glucan and a hydrophilic active agent, the glucan being at least partially cross-linked by a metaphosphate.

As used herein, the "nanoparticle" of the invention is a particulate matter, being a nanocapsule (NC) or a nanosphere (NS), which is biocompatible and sufficiently resistant to chemical and/or physical destruction, such that a sufficient amount of the nanoparticles remain substantially intact after administration into the human or animal body and for sufficient time to be able to reach the desired target tissue (organ). Generally, the nanoparticles are spherical in shape, having an average diameter of up to 700 nm. Where the shape of the particle is not spherical, the diameter refers to the longest dimension of the particle.

Depending on various parameters associated with the hydrophilic active agent (e.g. solubility, molecular weight, polarity, electrical charge, reactivity, chemical stability, biological activity, and others), the agent may be contained (encapsulated) in said nanoparticle, and/or embedded in the matrix making up the nanoparticle. For the chosen application, the nanoparticle may therefore be in the form of core/shell (termed hereinafter also as nanocapsule), having a polymeric shell and a core containing at least one hydrophilic active agent.

Alternatively, the nanoparticles may be of a substantially uniform composition not featuring a distinct core/shell structure. These nanoparticles are herein referred to as nanospheres (NSs).

In some embodiments, the nanoparticle is selected from a nanosphere and a nanocapsule.

In other embodiments, the average diameter is between about 100 and 200 nm. In other embodiments, the average diameter is between about 200 and 300 nm. In further embodiments, the average diameter is between about 300 and 400 nm, the average diameters between 400 and 500 nm. In further embodiments, the average diameter is between about 600 and 700 nm.

In some other embodiments, the average diameter is between about 50 and 700 nm. In other embodiments, the average diameter is between about 50 and 500 nm. In other embodiments, the average diameter is between about 50 and 400 nm. In further embodiments, the average diameter is between about 50 and 300 nm. In further embodiments, the average diameter is between about 50 and 200 nm. In further embodiments, the average diameter is between about 50 and 100 nm.

The nanoparticles may each be substantially of the same shape and/or size. In some embodiments, the nanoparticles have a distribution of diameters such that no more than 0.01 percent to 10 percent of the particles have a diameter greater than 10 percent above or below the average diameter noted above, and in some embodiments, such that no more than 0.1, 0.2, 0.4, 0.6, 0.8, 1, 2, 3, 4, 5, 6, 7, 8, or 9 percent of the nanoparticles have a diameter greater than 10 percent above or below the average diameters noted above.

The "water-soluble protein" is a protein belonging to a class of proteins having a structure permitting formation of dipole-dipole interactions with solvation medium, i.e. water, rendering the protein water-soluble. The protein may be linear, or of globular structure (i.e. having spherical quaternary structures in which hydrophobic amino acids are oriented towards the structure's interior while the hydrophilic amino acids are oriented outwards).

In some embodiments, the water-soluble protein is albumin.

In other embodiments, the albumin may be selected from human serum albumin (HSA) and bovine serum albumin (BSA).

"Glucan", as used herein, is meant to encompass a polysaccharide of sugar monomers linked together by glycosidic bonds. The glucan may be α- or β-glucan and may be of natural, synthetic or semi-synthetic origin.

In some embodiments, the glucan is an α-glucan.

The at least one glucan may be a combination (e.g., a mixture) of two or more glucans. The at least one glucan may be one or more of the glucans known in the art. Non-limiting examples of the at least one glucan are oxidized cellulose, pullulan, starch, glycogen, dextran, lichenin, mannan, galactomannan, arabinoxylan, galacton and any derivative thereof.

In some embodiments, the at least one glucan is dextran.

In other embodiments, the glucan may have a molecular weight of between about 5 KDa (kiloDalton) and 2,000 KDa.

In the nanoparticle of the invention, the glucan is "at least partially cross-linked"; at least some of the molecules of the glucan are inter-connected via a cross-linking agent to form a 3-dimensional structure. The glucan may be at least 1% cross-linked (i.e., 1% of all —OH groups of the glucan are bonded to the cross-linking agent), at least 2% cross-linked, at least 5% cross-linked, at least 10% cross-linked, at least 20% cross-linked, or even at least 30% cross-linked.

The cross-linking may be by any known cross-linking agent. In some embodiments, the cross-linking is achieved by the use of a metaphosphate. In some embodiments, cross-linking may be achieved by employing a combination of cross-linking agents, at least one of which being a metaphosphate agent.

In some embodiments, one or more metaphosphates are used as cross-linking agents to at least partially cross-link the glucan. The term "metaphosphate" is meant to encompass an oxyanion having the empirical formula $PO_3^-$, and may be described as having a structure made up of $PO_4$ structural units. In some embodiments, the metaphosphate is selected from sodium trimetaphosphate (STMP), sodium triphosphate pentabasic (STPP), and phosphorous oxychloride ($POCl_3$).

In some embodiments, the metaphosphate is sodium trimetaphosphate (STMP), having the formula:

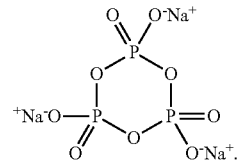

Without wishing to be bound by theory, the STMP reacts only with the hydroxyl (—OH) groups of the glucan. Unlike the typical cross-linking agents used for similar systems, such as gluaraldehyde, STMP does not bind to —$NH_2$ groups. Thereby hindrance of the activity of the hydrophilic active agent due to undesired binding is prevented, while maintaining the formation of a cross-linked nanoparticle used as a carrier and/or protecting vessel for the active compound. The crosslinked glucan thus forms a particulate structure for carrying the protein (i.e., albumin); while the protein, in turn, serves as a carrier and protection layer of the hydrophilic active agent.

In some embodiments, the ratio between the glucan (e.g. dextran) and the metaphosphate (e.g. STMP) is between 1:10 and 3:4 w/w). In other embodiments, this ratio may be 1:1, 1:2, 1:4, 1:10, 2:1 and 3:4 (w/w), glucan (e.g. dextran) to metaphosphate (e.g. STMP).

As stated above, the nanoparticles of the invention comprise also at least one "hydrophilic active agent". The hydrophilic active agent may be selected amongst active hydrophilic drugs used for the treatment or prevention of a disease or disorder in a subject (human or non-human). The active drug may be selected, in a non-limiting fashion, from a vitamin, a protein, an anti-oxidant, a peptide, a polypeptide, a lipid, a carbohydrate, a hormone, an antibody, a monoclonal antibody, a vaccine, a prophylactic agent, a diagnostic agent, a contrasting agent, a nucleic acid, a nutraceutical agent, a small molecule of a molecular weight of less than about 1,000 Da or less than about 500 Da, an electrolyte, a drug, an immunological agent and any combination of the aforementioned.

In some embodiments, the hydrophilic active agent may be selected amongst hormones.

In some embodiments, the hydrophilic active agent is selected from insulin, exenatide, growth hormone (e.g. somatotropin), octreotide acetate, lanreotide acetate, goserolin acetate, copaxone, etanercept, or monoclonal antibodies such as cetuximab, trastuzumab, adalimumab, bevacizumab, and others.

In some embodiments, the hydrophilic active agent has —$NH_2$ terminal moieties or —$NH_2$ pending moieties. As STMP does not react with the —$NH_2$ groups of such hydrophilic active agents, no cross-linking or any chemical reaction between the STMP and the active agent may occur during the cross-linking process. This results in the encapsulation of the active agent within the nanoparticle without damaging or affecting its activity and/or structure.

The nanoparticles of the invention may be used as delivery vehicles for a wide range of hydrophilic active agents topically, ocularly, orally, by inhalation, nasally, or parenterally into the circulatory system. The nanoparticle delivery systems of the invention facilitate targeted drug delivery and controlled release applications, enhance drug bioavailability at the site of action also due to a decrease of clearance, reduce dosing frequency, and minimize side effects. The nanoparticles of the invention may be used in the form of a dry powder (to be administered as is, e.g. for inhalable compositions), or may be reconstituted in an aqueous medium to form injectable formulations.

Where required, in order to provide further protection and stabilization of the active compound against different environments, the nanoparticles of the invention may be further encapsulated into larger particles, i.e. nanocapsules for parenteral administration or microparticles for oral administration.

Thus, in another one of its aspects, the invention provides a carrier comprising a hydrophobic polymer and a plurality of nanoparticles of the invention as defined herein, the plurality of nanoparticles being (i) encapsulated by a hydrophobic polymer, e.g. PLGA (namely forming double nano-encapsulation); or (ii) embedded in a matrix, such as a matrix formed of a hydrophobic polymer blend. Such a polymeric blend may be an Eudragit:HPMC blend, in which the Eudragit has pH-dependent solubility, while HPMC is aqueous soluble irrespective of the pH.

Such further encapsulation may result in a variety of structures comprising the nanoparticles. For example, when the nanoparticle is a nanosphere, the hydrophobic polymer may encapsulate the nanospheres by the formation of an outer shell, i.e. forming a nanocapsule comprising nanospheres (primary NS in secondary NC). Alternatively, the hydrophobic polymer may be in the form of a matrix in which the nanospheres are embedded (primary NS in secondary microsphere).

Similarly, when the nanoparticle is a nanocapsule, the hydrophobic polymer may encapsulate the nanocapsule (primary NC in secondary NC), or may be in the form of a matrix (primary NC in secondary microsphere).

In some embodiments, the drug-carriers may be in a form selected from nanocapsules, nanospheres and mixtures thereof.

The term "hydrophobic polymer" refers to a polymeric material which has little or no tendency to absorb water. Without wishing to be bound by theory, such polymers serve as a protective layer or a matrix for delivery of the hydrophilic active agents within aqueous environments. The hydrophobic polymers may also be used to render the carriers of the invention with slow-release or controlled-release characteristics, releasing the hydrophilic active agent in a predetermined way.

In some embodiments, the hydrophobic polymer is selected from poly(lactic glycolic) acid (PLGA), polymethyl-methacrylate (PMMA), hydroxypropyl methylcellulose (HPMC), poly(lactic acid) (PLA), poly(lacto-co-glycolide) (PLG), poly(lactide), polyglycolic acid (PGA) and poly(hydroxybutyrate).

In some embodiments, the hydrophobic polymer is selected from poly(lactic glycolic) acid (PLGA), poly(lactic acid) (PLA) and poly(lacto-co-glycolide) (PLG).

The carriers may be typically of a generally spherical shape, having, in some embodiments, a diameter of between about 200 to 900 nm. In other embodiments, the diameter of the carrier may be between about 200 and 800 nm, between about 200 and 700 nm, between about 200 and 600 nm, or between 200 and 500 nm. In some other embodiments, the diameter of the carrier may be between about 300 and 900 nm, between about 400 and 900 nm, between about 500 and 900 nm, between about 600 and 900 nm or between about 700 and 900 nm.

The nanoparticles and/or carriers of the invention may be formulated into pharmaceutical compositions. Thus, in another aspect, the invention provides a pharmaceutical composition comprising a nanoparticle and/or a carrier of the invention as herein described.

In another aspect, a delivery system of a hydrophilic active agent is provided, the delivery system comprising a hydrophobic polymer, and a plurality of nanoparticles as herein described encapsulated within said hydrophobic polymer.

A further aspect of the invention provides a delivery system of a hydrophilic active agent, comprising a hydrophobic polymer forming a matrix, and a plurality of nanoparticles as herein described embedded within said matrix.

The delivery system of the invention is suitable for delivering the active agent at a rate allowing controlled release of the agent over a period of time, such as at least about 12 hours, or in some embodiments, at least about 24 hours at least 7 days, or even at least 2 weeks. As such, the delivery system may be used for a variety of applications, such as, without limitation, drug delivery, gene therapy, medical diagnosis, and for medical therapeutics for, e.g., skin pathologies, cancer, pathogen-borne diseases, hormone-related diseases, reaction-by-products associated with organ transplants, and other abnormal cell or tissue growth.

The concentration of nanoparticles and/or carriers in a pharmaceutical composition may be selected so that the amount is sufficient to deliver a desired effective amount of the hydrophilic active agent to the subject, and in accordance with the particular mode of administration selected. As known, the "effective amount" for purposes herein may be determined by such considerations as known in the art. The amount must be effective to achieve the desired therapeutic effect, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, the effective amount depends on a variety of factors, inter alia, its distribution profile within the body, a variety of pharmacological parameters such as half life in the body, on undesired side effects, if any, on factors such as age and gender, and others.

The pharmaceutical composition may further comprise pharmaceutically acceptable additives, which may be, for example, vehicles, adjuvants, excipients, or diluents, and are well-known to those who are skilled in the art and are readily available to the public. It is of note that the pharmaceutically acceptable additive be one which is chemically inert to the active agent and one which has no detrimental side effects or toxicity under the conditions of use. In addition, the composition may contain other standard additives such as an emollient, moisturizer, thickener, emulsifier, neutralizer, coloring agent, a fragrance, absorber or filter, preservative and/or gelling agent.

In some embodiments, the pharmaceutical composition is adapted for topical, oral, inhalation, nasal, transdermal, ocular or parenteral administration of said hydrophilic active agent. In other embodiments, the pharmaceutical composition is adapted for oral administration of said hydrophilic active agent. In some other embodiments, the pharmaceutical composition is adapted for administration of said hydrophilic active agent by injection.

The choice of additives will be determined in part by the particular active agent, as well as by the particular method used to administer the composition or the delivery system.

Pharmaceutical compositions suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; and (c) powders; Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The nanoparticles of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer Compositions suitable for parenteral administration include aqueous isotonic sterile injection solutions, which can contain anti-oxidants, buffers, bacteriostats, and solutes that render the formulation isotonic with the blood of the intended recipient, and aqueous sterile suspensions that include suspending agents, solubilizers, thickening agents, stabilizers, and preservatives. The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use.

The compositions of the present invention may be made into injectable formulations. The requirements for effective pharmaceutical carriers for injectable compositions are well known to those of ordinary skill in the art.

The term "topical" as used herein refers to the application of a composition according to the invention directly onto at least a portion of a subject's skin (human's or non-human's skin) so as to achieve a desired effect, e.g., cosmetic or therapeutic effect, at the site of application.

The nanoparticles, carriers and/or delivery systems of the invention can be administered in a biocompatible aqueous solution. This solution can be comprised of, but not limited to, saline, water or a pharmaceutically acceptable medium.

The administration of delivery system formulation can be carried out at a single dose or at a dose repeated once or several times after a certain time interval. The appropriate dosage may vary according to such parameters as the therapeutically effective dosage as dictated by and directly dependent on the individual being treated, the mode of administration, the unique characteristics of the therapeutic agent and the particular therapeutic effect to be achieved. Appropriate doses can be established by the person skilled in the art.

In some embodiments, the delivery system may be further encapsulated within a biodegradable capsule, typically for oral administration. In such embodiments, said biodegradable capsule is in the form of an entero-coated capsule.

In some other embodiments, the delivery system is adaptable for a facilitated targeted therapeutic delivery and controlled release administration of said hydrophilic active agent.

Another aspect of the invention provides the use of a nanoparticle or a carrier of the invention as described herein, for the preparation of a pharmaceutical composition for treating a disease, disorder or a chronic condition. Non-limiting examples of chronic conditions are diabetes, obesity, hormone deficiencies, protein deficiencies, etc. As the particles of the invention provide extended release of the active agent (for example a hormone or a protein), administration of these nanoparticles of the invention may reduce the number of required routine treatments, thereby resulting in improving patient's quality of living as well as increasing patient compliance to the treatment.

The term "treatment" or any lingual variation thereof, as used herein, refers to the administering of a therapeutic amount of the nanoparticle or delivery system of the present invention which is effective to ameliorate undesired symptoms associated with a disease, to prevent the manifestation of such symptoms before they occur, to slow down the progression of the disease, slow down the deterioration of symptoms, to stabilize a chronic condition, to enhance the onset of remission period, slow down the irreversible damage caused in the progressive chronic stage of the disease, to delay the onset of said progressive stage, to lessen the severity or cure the disease, to improve survival rate or induce more rapid recovery, or to prevent the disease from occurring or a combination of two or more of the above.

In another aspect, there is provided a process for the preparation of a nanoparticle comprising a water-soluble protein, a glucan and a hydrophilic active agent, the glucan being at least partially cross-linked by a metaphosphate, the process comprising:

delivering (e.g., by injection) an organic solvent into a mixture containing a first aqueous solution comprising said water-soluble protein and said glucan and a second aqueous solution comprising said hydrophilic active agent; and adding said metaphosphate to said mixture to thereby at least partially cross-link said glucan for obtaining said nanoparticle.

In some embodiments, the process comprising:

obtaining a mixture of a first aqueous solution comprising said water-soluble protein and said glucan and a second aqueous solution comprising said hydrophilic active agent;

delivering (e.g., injecting) an organic solvent into said mixture; and adding said metaphosphate to said mixture to thereby at least partially cross-link said glucan for obtaining said nanoparticle.

In further embodiments, the process comprising:

mixing a first aqueous solution comprising said water-soluble protein and said glucan with a second aqueous solution comprising said hydrophilic active agent to obtain a mixture;

delivering (e.g., injecting) an organic solvent into said mixture; and adding said metaphosphate to said mixture to thereby at least partially cross-link said glucan for obtaining said nanoparticle.

In further embodiments, the organic solvent is delivered into the mixture by injection.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
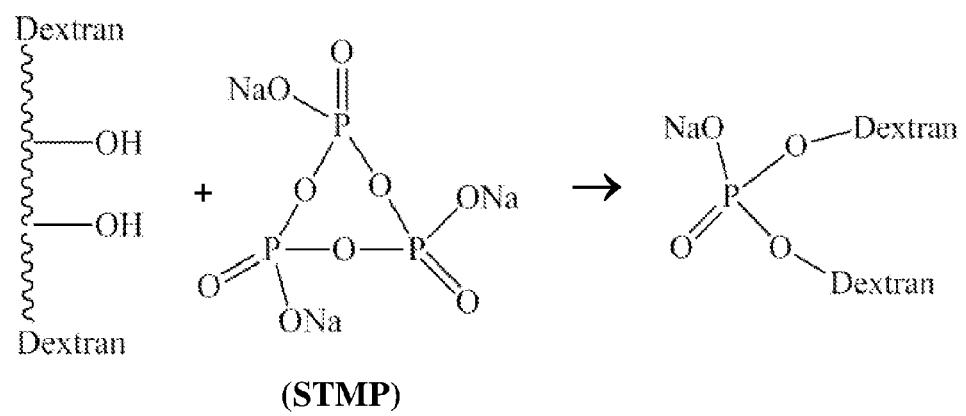
FIG. 1A is a schematic description of a cross-linking mechanism of dextran by STMP.

Exenatide is a synthetic version of exendin-4, a hormone found in the saliva of the Gila monster that displays biological properties similar to human glucagon-like peptide-1 (GLP-1), a regulator of glucose metabolism and insulin secretion. The incretin hormones, GLP-1 and glucosedependent insulinotropic peptide (GIP), are produced by the L and K endocrine cells of the intestine following ingestion of food. GLP-1 and GIP stimulate insulin secretion from the beta cells of the islets of Langerhans in the pancreas. Although only GLP-1 causes insulin secretion in the diabetic state, it is ineffective as a clinical treatment for diabetes as it has a very short half-life (a few minutes) in vivo.

Exenatide is a 39-amino-acid peptide, an insulin secretagogue, with glucoregulatory effects. The medication is injected subcutaneously twice a day using a filled pen device. Exenatide bears a 50% amino acid homology to GLP-1, is structurally analogous to GLP-1, and has a longer half-life (2.4 h) in vivo. Thus, it was tested for its ability to stimulate insulin secretion and lower blood glucose in mammals, and was found to be effective in the diabetic state. In studies on rodents, it has also been shown to increase the number of beta cells in the pancreas.

Exenatide raises insulin levels quickly (within about ten minutes of administration) with the insulin levels subsiding substantially over the next hour or two. Exenatide has been approved as an adjunctive therapy for patients with type 2 diabetes failing to achieve glycemic control with oral antidiabetic agents. A dose taken after meals has a much smaller effect on blood sugar than one taken beforehand. The effects on blood sugar diminish after six to eight hours. The medicine is available in two doses: 5 µg and 10 µg. Treatment often begins with the 5 µg dosage, which is increased if adverse effects are insignificant. According to the manufacturer, the autoinjector must be stored in a refrigerator between 2 and 8° C. before first use, and then at a temperature between 2 and 25° C. In hot weather, therefore, it should be continuously refrigerated. It should be emphasized that a potential disadvantage in exenatide clinical applications is the frequent subcutaneous (SC) injections required. SC injections can cause pain, side effects and possible infections at the sites of injection that could adversely affect patient compliance.

A long-acting release form of exenatide has been developed for use as a once-weekly injection. This sustained-release formulation consists of injectable microspheres of exenatide and poly (D,L lactic-co-glycolic acid), a common biodegradable polymer with established use in absorbable sutures and extended-release pharmaceuticals, that allows gradual drug delivery at a controlled rate. Thus, exenatide extended release is a useful option for the treatment of type 2 diabetes, particularly in patients where bodyweight loss is an essential aspect of the individual patient's management. However, it is still an injection and need to be injected once weekly.

Exenatide and insulin are hydrophilic biomacromolecules which exhibit low oral human bioavailability (estimated at less than 2%) following extrapolation from data regenerated in animals, which has been attributed to proteolytic instability and limited ability to permeate through biological membranes.

In the present invention, encapsulation of hydrophilic macromolecules is demonstrated for exenatide and insulin. The first objective is entrapment of exenatide in the matrix of the nanoparticles at a reasonable level, with an aim at increasing the loading of the nanoparticles in the microparticles for oral administration, in order to ensure that the drug content in the final powdered formulation is the highest possible.

The present invention further provides the incorporation of peptidic drugs into primary nanocapsules or nanoparticles that are further embedded in larger nanocapsules, resulting in the formation of double-coated nanoparticulate delivery systems that are designed to protect the peptide from the detrimental effects of the external environmental for prolonged release using parenteral route of administration. Peptide loaded primary nanocapsules are encapsulated within larger secondary nanocapsules. It should be noted that in a nanocapsule having a diameter of 400 or 600 nm, it is theoretically possible to incorporate at least 64 and 216 nanocapsules of 100 nm diameter respectively based on volume calculations.

The secondary microparticles, i.e. carriers encapsulating the primary nanoparticles of the invention, were obtained by a spray drying technique. Spray drying is a process that converts liquids or suspensions into dry powders at a continuous single step process. Spray drying was carried out by using Buchi laboratory scale spray dryers that can generate microparticles in the size range of 1000 nm to 20 µm for small samples quantities (few milligrams or milliliters) at high yields (>70%), thereby forming microparticles at a relatively high yield. The secondary microparticles generally have a size (diameter) of between 1 and 30 microns.

Materials

Bovine serum albumin (BSA) and Dextran 12 KDa were purchased from Sigma-Aldrich (Rehovot, Israel). Exenatide was kindly donated by Teva Pharmaceuticals (Jerusalem, Israel). Glutaraldehyde 8% in water was purchased from Sigma-Aldrich (Rehovot, Israel). Sodium trimetaphosphate (STMP) was purchased from Alfa Aesar (Haverther chemicals and hill, MA, USA). Poly(methacrylic acid, Ethyl acrylate 1:1 (Eudragit® L100-55) was obtained from Rohm (Dramstadt. GmbH, Germany). Hydroxypropylmethylcellulose (Methocel E4M Premium) was purchased from Dow Chemical Company (Midland, Mich., USA). Sodium phosphate monobasic, monohydrate was purchased from Mallinckrodt chemicals (Phillipsburg, N.J., USA). All organic solvents were HPLC grade and purchased from J.T. Baker (Deventer, Holland).

Preparation of Primary NPs

The first line of protection on the sensitive biomacromolecule, exenatide, was achieved by loading the peptide into primary BSA NPs. Two different types of NPs were prepared: BSA NPs cross-linked with glutaraldehyde 8% and BSA combined with dextran 12 KDa NPs cross-linked with STMP.

BSA NPs Cross-Linked with Glutaraldehyde

The BSA NPs cross-linked with glutaraldehyde, were prepared by an established desolvation method as previously described by Weber et. al [ref-Desolvation process and surface characterisation of protein nanoparticles]. 200 mg of BSA and 4 or 8 mg of exenatide were dissolved in 20 ml of bi-distilled water (DDW). After 0.5 hour, the pH of the solution was adjusted to 8.5 by 0.1M NaOH. Then, 40 ml of acetone were slowly added to the aqueous phase. An o/w emulsion was formed as evidenced by the rapid formation of opalescence in the dispersion medium. BSA NPs were then cross-linked using 12.5 µl of glutaraldehyde 8% solution over 2 hours. Following cross-linking reaction completion, the acetone was evaporated under laminar air flow. This formulation was denominated Glut-1.

BSA/Dextran NPs Cross-Linked with STMP

The BSA/dextran NPs were similarly prepared by dissolving in 20 ml DDW, the following compounds: 200 mg of BSA, 50 mg of dextran 12 KDa and 4 or 8 mg of exenatide when needed. After 0.5 hour, the pH of the solution was adjusted to 8.5 by 0.1M NaOH to make sure that the adjacent hydroxyl groups on dextran are available for the reaction with the STMP cross-linker. Then, 20 ml of acetone were slowly added to the aqueous phase. BSA/dextran NPs were then cross linked using 50 mg of STMP over 3 hours and acetone was evaporated as described above. Preliminary formulations were prepared and evaluated by varying the process parameters. Two formulations that differ in the dextran amount were selected for further animal studies: 50 and 150 mg. The formulation with 50 mg was denominated as DX-50- and 150 mg as DX-150.

Microspheres (MPs) Preparation

The microspheres (MPs) were formed by microencapsulating the exenatide containing NPs using the spray drying technique. For the purpose of microencapsulation, 100 ml of $NaH_2PO_4$ buffer was prepared. pH of the buffer was adjusted to 6.5 by 1M NaOH solution. An amount of 750 mg of Eudragit was dissolved in that solution maintaining pH at 6.5. In addition, 1% w/v hydroxypropylmethylcellulose (HPMC) solution was prepared by adding 1000 mg of HPMC to 100 ml of pre-heated (~80° C.) DDW. Then, the Eudragit solution was added via funnel with a gaza band (to filter Eudragit particles that might have not dissolved) to the HPMC solution.

Once the acetone was evaporated from the NPs suspension, the combined solution of the microparticle polymers was added to the NPs suspension. The suspension was then spray-dried with a Buchi mini spray-drier B-190 apparatus (Flawil, Switzerland) under the following conditions: inlet temperature 160° C.; outlet temperature 85° C.; aspiration 100%; feeding rate of the suspension was 7 ml/min; the powder was collected in the cyclone separator and the outlet yield was calculated.

Physicochemical characterization of the NPs and subsequent MPs

NPs Characterization

The mean diameter and zeta potential of the various NPs were characterized using Malvern's Zetasizer (Nano series, Nanos-ZS, UK) at 25° C. and using water as diluent. Morphological evaluation was performed using cryo-transmission electron microscopy (Cryo-TEM). In the Cryo-TEM method, a drop of the solution is placed on a carbon-coated holey polymer film supported on a 300-mesh Cu grid (Ted Pella Ltd., Redding, Calif., USA), and the specimen is automatically vitrified using Vitrobot (FEI) by means of a fast quench in liquid ethane to −170° C. The samples were studied using an FEI Tecnai 12 G2 TEM, at 120 kV with a Gatan cryo-holder maintained at −180° C., and images were recorded on a slow scan cooled charge-coupled device camera.

Extra High Resolution Scanning Electronic Microscopy (SEM) Studies of MPs

Morphological and size evaluation of spray dried MPs were carried out using Extra High Resolution Scanning Electron Microscopy (model: Magellan 400 L, FEI, Germany). The samples were fixed on a SEM-stub using double-sided adhesive tape and then made electrically conductive following standard coating by gold spattering (Pilaron E5100) procedure under vacuum.

Drug Content

The total amount of exenatide in the powder was analyzed by dissolving the sample in 2 ml of water overnight. Afterwards, the mixture was centrifuged at 14000 rpm for 2 min 1 ml from the supernatant was injected into HPLC under the following conditions: Column Restek Viva C4 (5 μm), 250/4.6 mm. Column temperature was kept at 45° C. Mobile phase A was acetonitrile (ACN), and mobile phase B was potassium dihydrogen phosphate ($KH_2PO_4$, 20 mmol/L) adjusted to pH 2.5 by phosphoric acid. The $KH_2PO_4$ buffer was filtered through a 0.2 μm membrane filter prior to use. The following gradient conditions were used for exenatide: from 30% to 45% mobile phase A in 15 min, and re-equilibrated back to 30% mobile phase A for 3 min. Flow rate was 1.5 mL/min. Injection volume was 20 μL. UV signal was detected at 215 nm. The exenatide content was calculated using a calibration curve constructed from exenatide concentrations ranging between 0 to 20 μg/ml that yielded a linear correlation ($r^2$=0.999).

Pharmacokinetic Studies in Rats

All the animal studies were approved by the local Ethical Committee of Laboratory Animal Care at The Hebrew University of Jerusalem (MD-13575-4). Sprague Dawley male rats (300-350 g) were used in this study. The animals were housed in SPF conditions, fasted and had free access to drinking water. Seven groups of 3 rats were randomly divided to evaluate the oral absorption and exenatide plasma levels over time. Exenatide was injected subcutaneously as a solution or formulated in Byetta® at a dose of 65 μg/kg (20 μg/rat). The third and fourth groups of rats were orally administrated with either 31 mg of blank MPs spiked externally with exenatide or exenatide solution at a dose of 165 μg/kg (50 μg/rat) to determine whether the blank formulation has an effect. Finally, 35, 33 and 32 mg of Glut-1, DX-50 and DX-150, respectively, were orally administrated at a dose of 165 μg/kg (50 μg/rat). All oral suspensions were dispersed in 2 mL DDW, while the volume of subcutaneous injection was 200 μl.

Blood samples (500 μl) were taken from the rat tail at 0, 0.5, 1, 2, 4, 6, 8 and 24 h. The blood samples were collected in EDTA and aprotinin containing tubes. The samples were centrifuged at 10,000 rpm, 4° C. for 10 min, after which 250 μl of plasma samples were transferred to new tubes and stored at −80° C. until analyzed. Exenatide levels were determined using CEK-0130-01 ELISA Kit (AB Biolabs, USA) following the protocol suggested by the company.

Bioavailability Calculations

The pharmacokinetic parameters were calculated using WinNonlin software, applying the trapezoid rule for calculation of AUC. The AUC values were adjusted following size dose corrections.

The relative bioavailability of the different oral formulations compared to the standard marketed formulation Byetta® injected subcutaneously was calculated using the following equation:

$$\text{Relative bioavailability} = \frac{[AUC\ \text{oral}]}{[AUC\ sc]} * 100$$

Exenatide Formulations

Figure 1B:
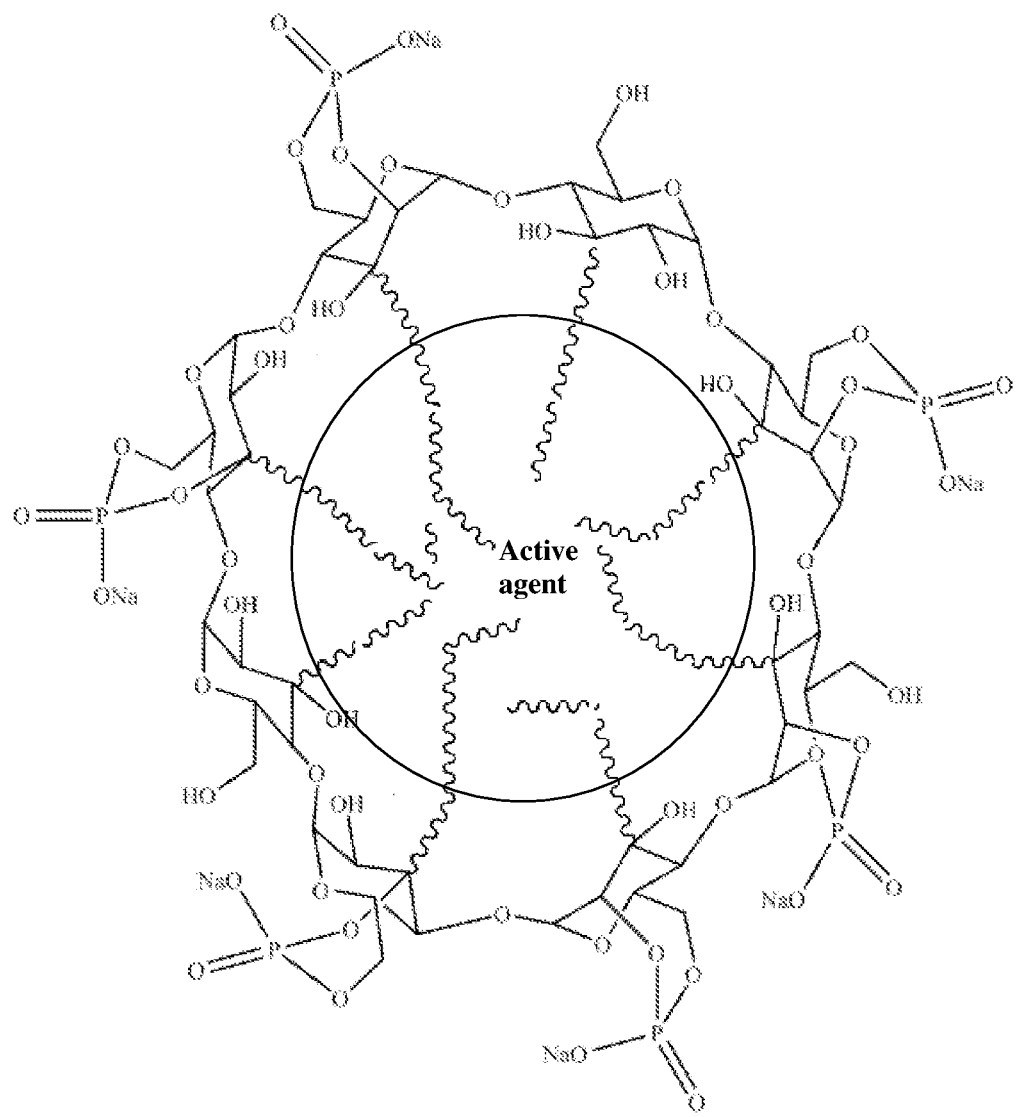
FIG. 1B is a schematic depiction of a cross-linked particle.

Formulation F-1: Exenatide Primary Nanoencapsulation with BSA and Cross-Linked Dextran 200 mg BSA (Sigma-A7906) and 50 mg of Dextran 12 KDa (Sigma-31418) were dissolved in 10 ml DDW. 4 mg of Exenatide were separately dissolved in 10 ml DDW. Albumin/Dextran solution was added to the Exenatide solution to complete peptide dissolution (solution A). The pH 6.8 was adjusted with NaOH 0.1M to reach pH of ~8.5. 20 ml acetone were injected to solution-A during strong stirring to elicit formation of BSA-Dextran NPs comprising most of Exenatide. Dextran cross-linking was obtained by addition of 5% (1 ml) of sodium trimetaphosphate (STMP) and the solution was agitated at 900 rpm at room temperature over 3 hours. A schematic representation of the synthesis of formulation F-1 is shown in FIGS. 1A-1B.

Figure 2:
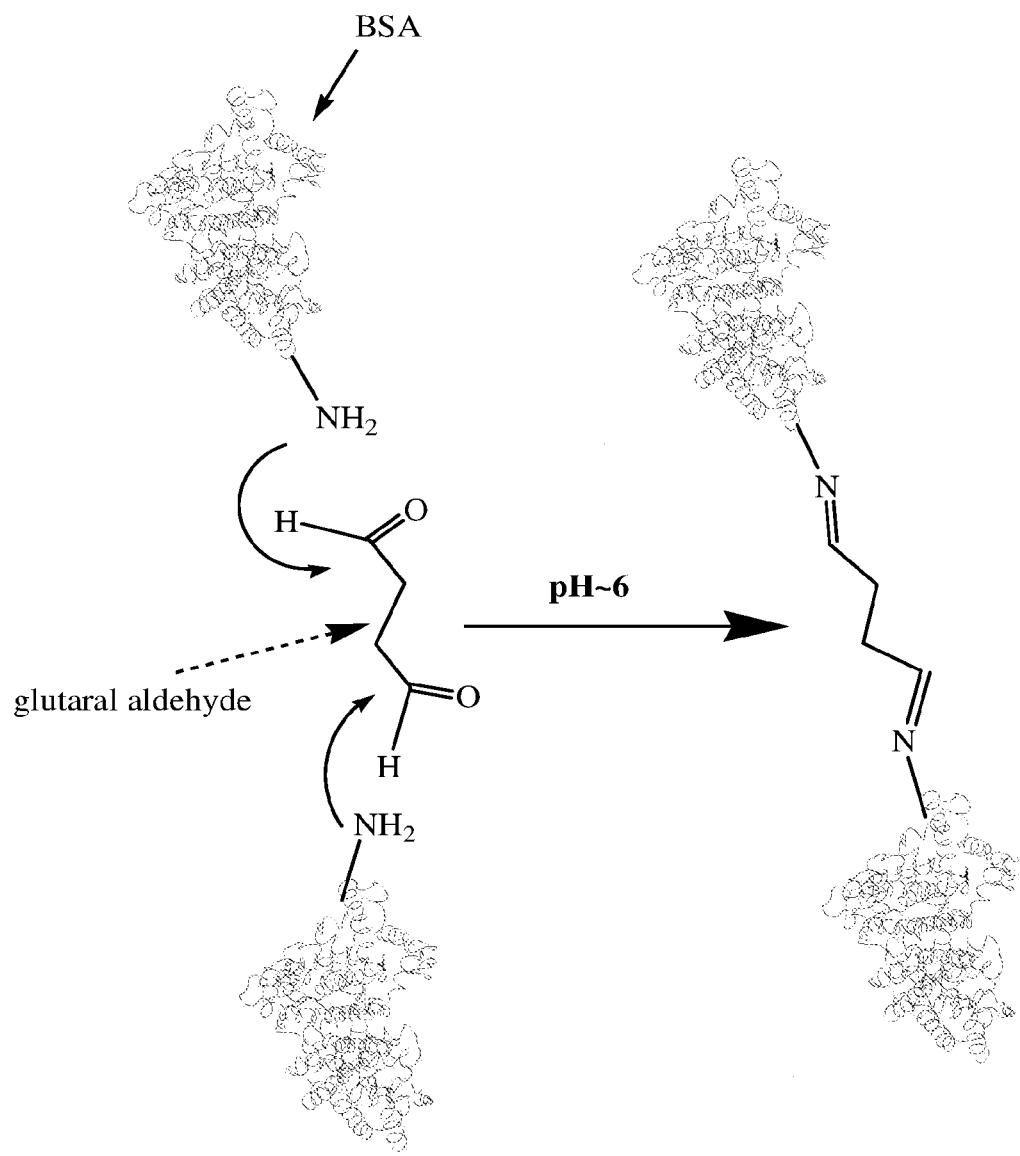
FIG. 2 shows the cross-linking reaction of albumin, rendering the albumin insoluble in aqueous solutions.

Formulation F-2: Exenatide Primary Nanoencapsulation with BSA and Crosslinked Glutaraldehyde 200 mg BSA (Sigma-A7906) were dissolved in 10 ml DDW. 4 mg of Exenatide were separately dissolved in 10 ml DDW. Albumin solution was added to the Exenatide solution to complete peptide dissolution. pH was adjusted with NaOH 0.1M to reach pH between of 8.5. 15 ml acetone were injected to solution-A during strong vortex to elicit formation of BSA-Exenatide NPs comprising most of Exenatide. BSA cross-linking was obtained by addition of 25 μl glutaraldehyde 4% and the solution was agitated at 900 rpm at room temperature over 3 hours. A schematic representation of cross linking of formulation F-2 is shown in FIG. 2.

Formulation F-3: Conjugation of Exenatide to Nanoparticles Surface

Exenatide activation was carried out by reacting 4 mg of Exenatide with the spacer sulfo-SMCC (Sulfosuccinimidyl-4-(N-maleimidomethyl)cyclohexane-1-carboxylate) for 2 hours at room temperature.

For preparing the nanoparticles, 150 mg PLGA (50K) (Resomer RG 504H, Boehringen Ingelheim), 150 mg PLGA-co-PEG (45K and 5K) (Resomer RGP d 50105) and 10 mg oleyl cysteinamide were dissolved in 50 ml acetone. 100 mg Solutol HS 15 (BASF) was dissolved in 100 ml DDW while stirring. The organic phase was added to the aqueous phase under stirring (900 rpm) and allowed to mix over 15 min. The formulation was evaporated to less that 10 ml on 37° C. using Rotor evaporator under reduced pressure. pH was adjusted to 6.7-6.8 using NaOH 0.1M and volume was adjusted to 10 ml. The formulation was centrifuged at 4000 rpm to sediment large particles (3-4%). Only the colloidal supernatant was used for final formulation.

The activated exenatide was incubated immediately with the preformed formulation. Incubation was performed at room temperature, overnight on magnetic stirrer. The maleimide groups of the LC-SMCC reacted with the sulfhydryl groups of the oleyl cysteinamide at pH=6.5-7.5 to form stable thioether bonds.

Formulation F-4: Exenatide Double Encapsulation 100 mg BSA (Sigma-A7906) were dissolved in 2 ml DDW. 5 mg of Exenatide were separately dissolved in 3 ml DDW. Albumin solution was added to the Exenatide solution to complete peptide dissolution. pH was adjusted with NaOH 1M to 7.4-8. 10 ml acetone was injected into the solution during strong stirring to elicit formation of BSA nanoparticles comprising most of Exenatide.

128 mg PLGA (50K) was dissolved in 93 ml acetonitrile. 6 ml of BSA nanoparticles formulation was added during stirring to form double encapsulation (nanospray conditions: 4 μm mesh, in temperature: 50° C.).

Microencapsulation of Formulations F1-F4 with Eudragit L and HPMC 500 mg of HPMC were dissolved in 100 ml preheated DDW, and 500 mg of Eudragit (anionic) were dissolved in 100 ml PBS.

To the nanoparticles solution, Eudragit solution and HPMC solution were added. The combined solutions were stirred for 30 minutes at 500 rpm in room temperature; the combined dispersion was evaporated by spray drier at the following conditions: inlet Temp=160° C.; Outlet Temp=100° C. Microparticles comprising drug-loaded nanoparticles were obtained.

The physicochemical characterization of the drug-loaded nanoparticles is shown in Table 1.

TABLE 1

Physicochemical properties of Exenatide formulations.

| Formulation | NPs formation method | Size (nm) | Zeta potential | PDI | % Yield (dry) |
|---|---|---|---|---|---|
| EXA-12 | BSA:Dextran (cross-linked) | 173.4 | −38.4 | 0.565 | 45.9 |
| F-1* | BSA:Dextran (cross-linked) | 83 | −28.3 | 0.51 | 25 |
|  |  | 359 | −33.5 | 0.306 | 44 |
| F-2 | BSA (cross-linked with glutaraldehyde) | 132.5 | −45 | 0.1 | 45 |
| F-3 | Peptide conjugated to PLGA (50K NPs) | 142.8 | −45 | 0.026 | 40 |
| F-4** | Double encapsulation | 163.1 | −48.6 | 0.093 | 43 |
|  |  | 88.29 | −54.4 | 0.048 | 63 |

*2 batches were united.
**for the unified formulation

Evaluation of Glucose Lowering Effect of Exenatide in Various Formulations (F1-F5) on OB/OB Mice Acclimation of the mice for few days was carried out by giving glucose and monitored glucose levels over 6 hours. Afterwards, all mice were injected with Byetta (commercial exenatide injectible formulation) at a dose of 20 μg/kg and monitoring blood glucose levels over 6 hours.

Evaluation of the glucose lowering effect of Exenatide in various formulations on OB/OB mice was carried out for a group size of n=8 per group of animals. Each group of OB/OB mice was provided with one of the following:
  i) Saline+empty vehicle (F-5)
  ii) Byetta-injection
  iii) Exenatide (F-1)
  iv) Exenatide (F-2)
  v) Exenatide (F-3)
  vi) Exenatide (F-4)

On 1st day, all animals were fasted 18 hours prior to the experiments then after fasting, blood glucose was monitored. Glucose was injected (18 mm/kg) by i.p. to all animals; 60 min after glucose injection the following parameters were examined: blood glucose measurement, blood collection for Elisa, body weight measurement. Then, Formulations F1-F5 were orally administered (Byetta was administered by s.c.). After administration, blood glucose levels were monitored at 30 min, 1 hr, 1.5 hr, 2 hr, 3 hr and 6 hr from administration.

From 2nd day to 9th day, body weight was measured at time zero and blood was collected for ELISA. This was followed by administration of the formulations, and measuring blood glucose levels within 1 hr from drug administration (as well as blood collection for ELISA).

On 10th day, prior to administration the last doses of the tested formulations, glucose was given again followed by body weight measurement and blood collection of for ELISA. After this, the formulations were administered in double dose (to check the potentiation of these formulations) to the respective animals and then after 1 hr of drug administration, blood glucose levels were measured and blood was collected for ELISA.

Body Weight Measurements

Figure 3:
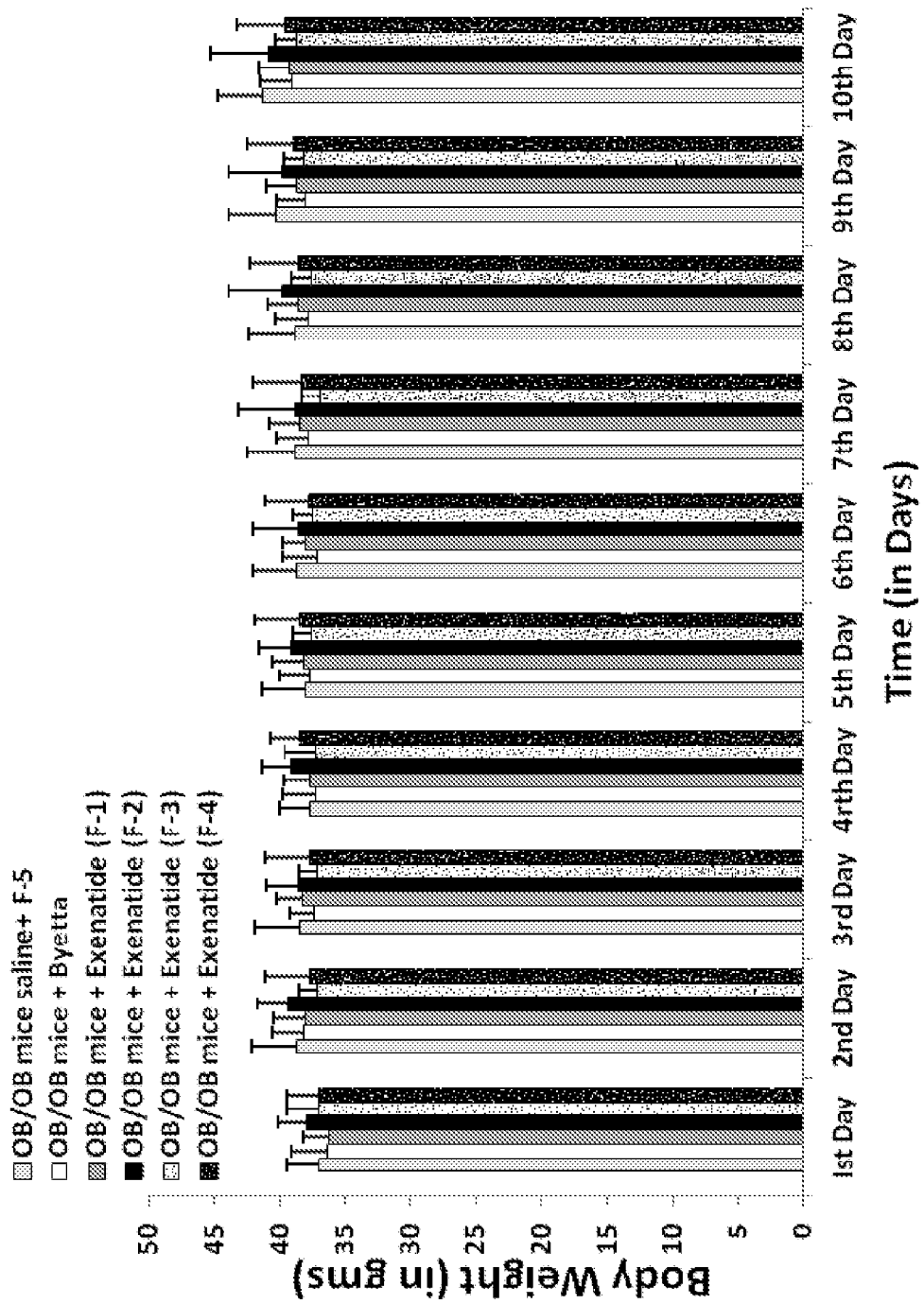
FIG. 3 shows body weight results for different formulation of Exenatide (FI-V) and Byetta.

Body weight measurements were carried out at the same time for each mouse. The results of the different formulation of Exenatide (F1-F5) and Byetta are shown in FIG. 3.

Blood Glucose Levels Measurements

Figure 4:
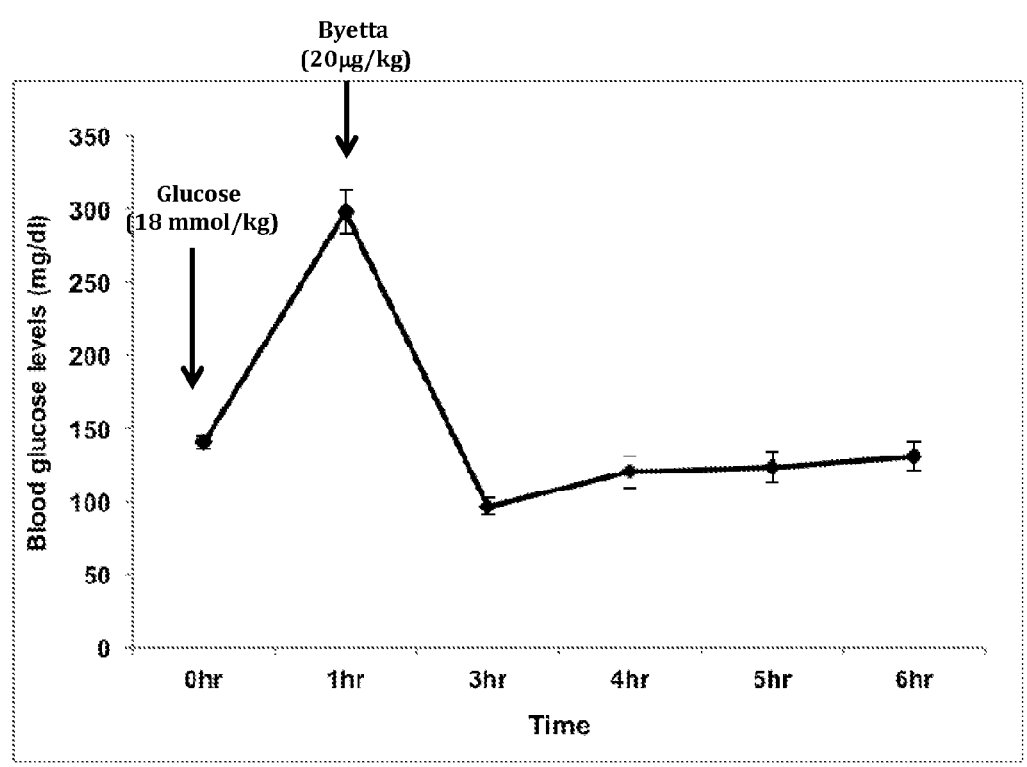
FIG. 4 shows the blood glucose levels from preliminary experiments with Byetta.
Figure 5:
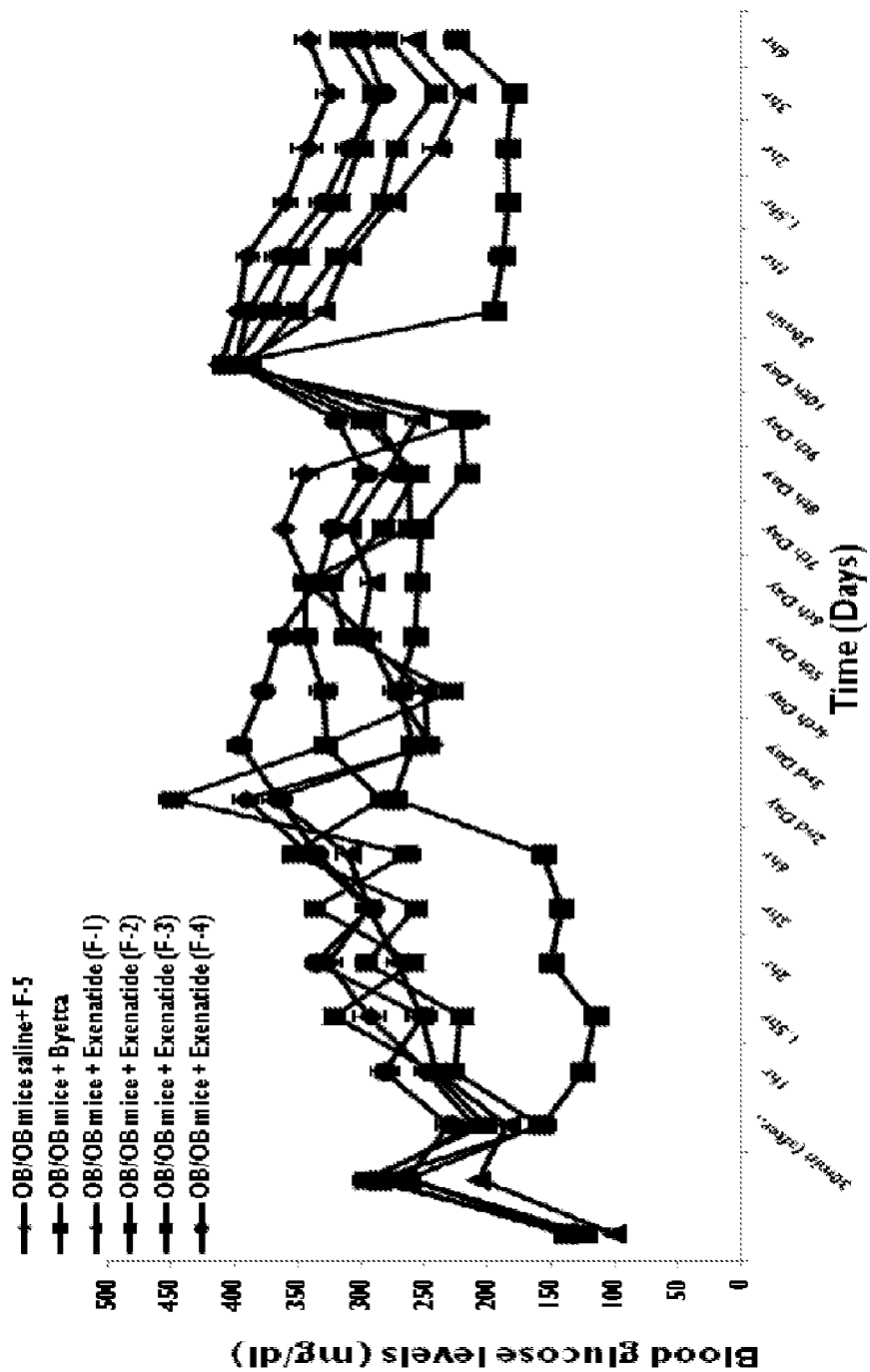
FIG. 5 shows the blood glucose levels from different formulation of Exenatide (FI-V) and Byetta.

Blood samples were collected on day 1 to 10. Animals at 15-19 weeks of age were fasted overnight (up to 16 h) prior to blood glucose measurement procedures, by transferring mice to a clean cage base with clean nesting material and a small amount of soiled bedding and environmental enrichment from their old cage. The change of cage and bedding obviated the possibility that mice may access spilled food. Water remained freely available throughout the entire fasting period. Food was returned following collection of the final blood sample. A drop of blood was obtained from unrestrained mice by nicking the tail tip with a blade. Measurements were taken using a handheld blood glucose meter (Accu-chek Aviva, Roche Diagnostics, UK). The blood glucose levels from preliminary experiments with Byetta are shown in FIG. 4, while the blood glucose levels for different formulation of Exenatide (F1-F5) and Byetta are shown in FIG. 5.

Plasma Insulin Levels

Figure 6:
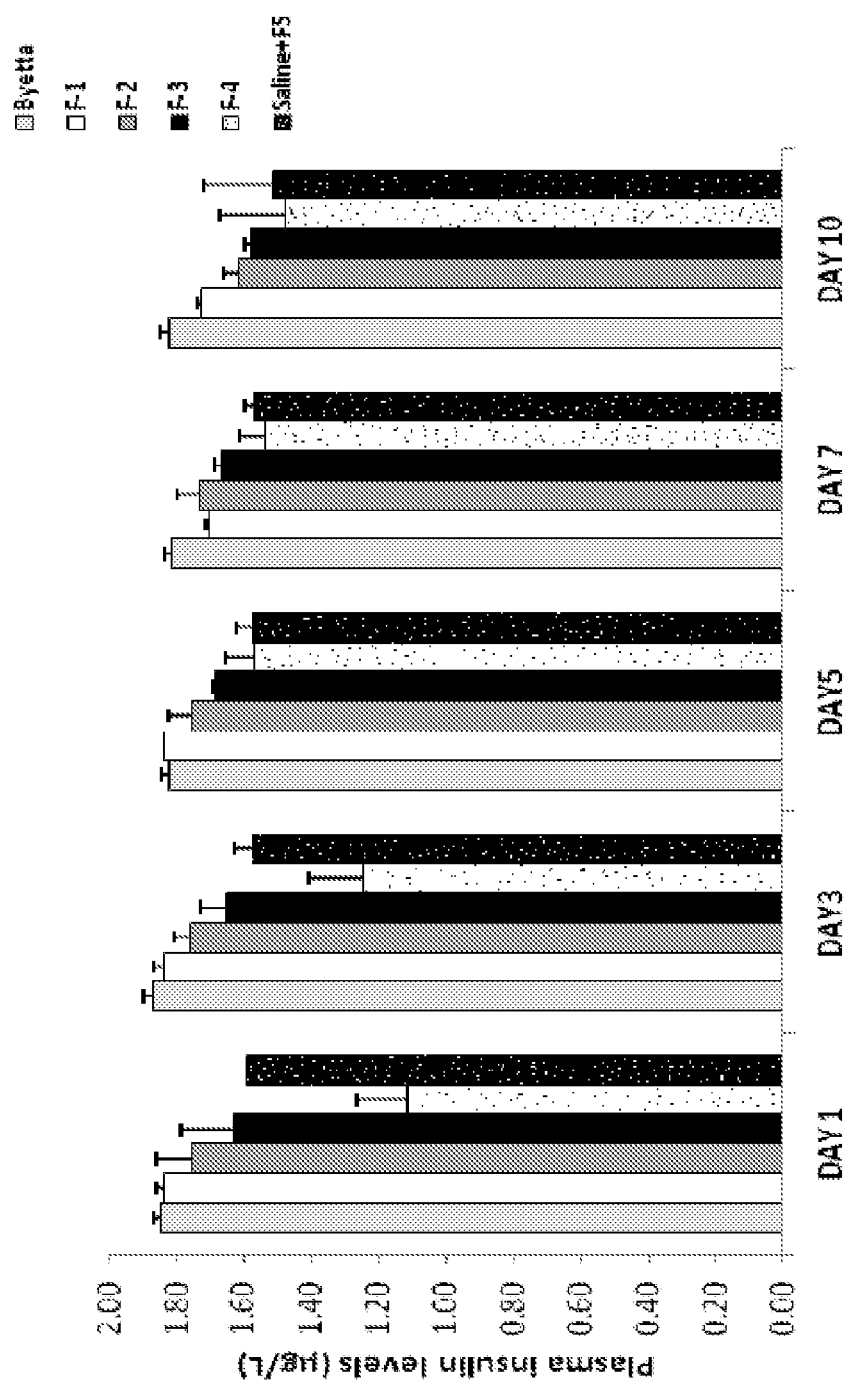
FIG. 6 shows the plasma insulin levels of the different groups at different days.

For insulin determination, 150 mL of blood was sampled from the tail vein (blood was processed in a centrifuge at 3000 cycles/min for 10 and 5 min). Blood plasma was separated into two heparin-coated tubes for blood parameters and insulin measurements (30 mL each). Plasma insulin levels were measured using a mouse insulin enzyme-linked immunosorbent assay kit (Mercodia, Sylveniusgatan, Sweden). The plasma insulin levels of the different groups at different days are shown in FIG. 6.

Glycosylate Hemoglobin Levels

Figure 7A:
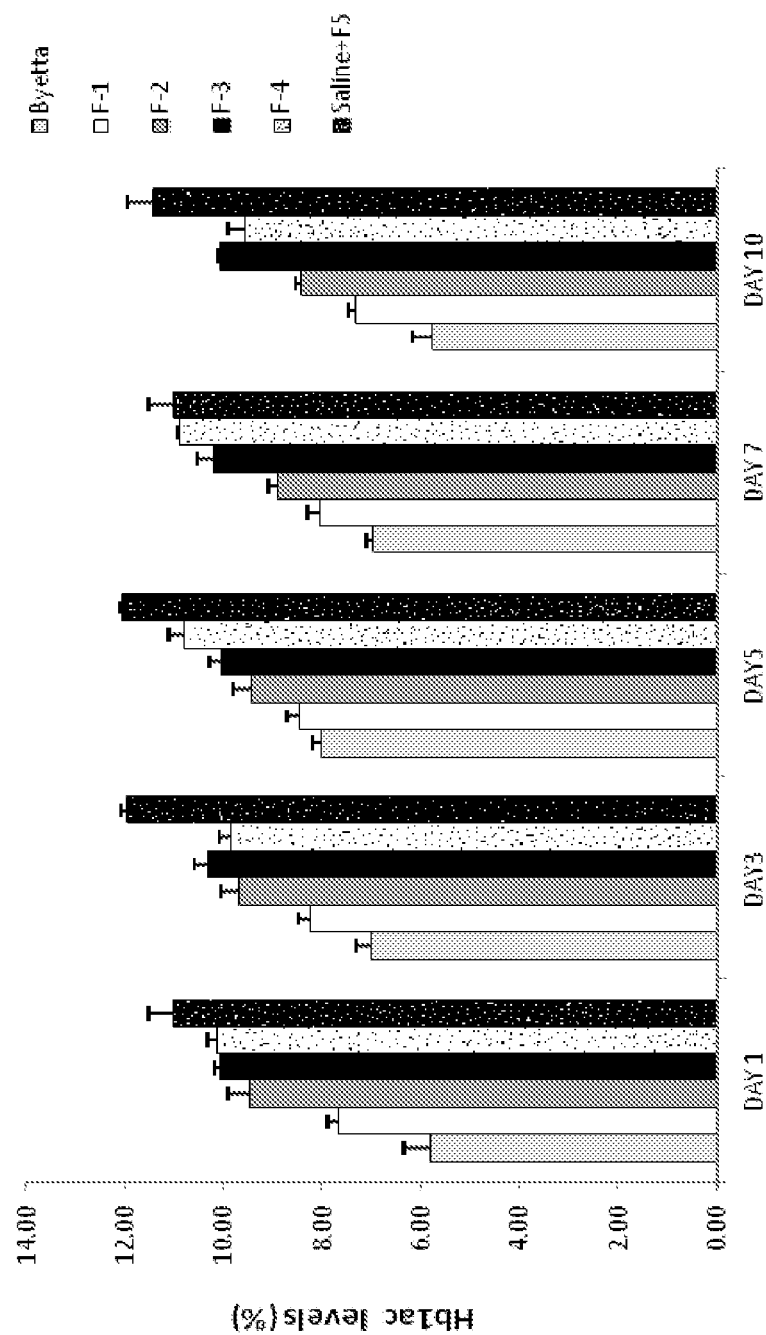
FIG. 7A shows the glycosylate hemoglobin levels of the different groups at different days.
Figure 7B:
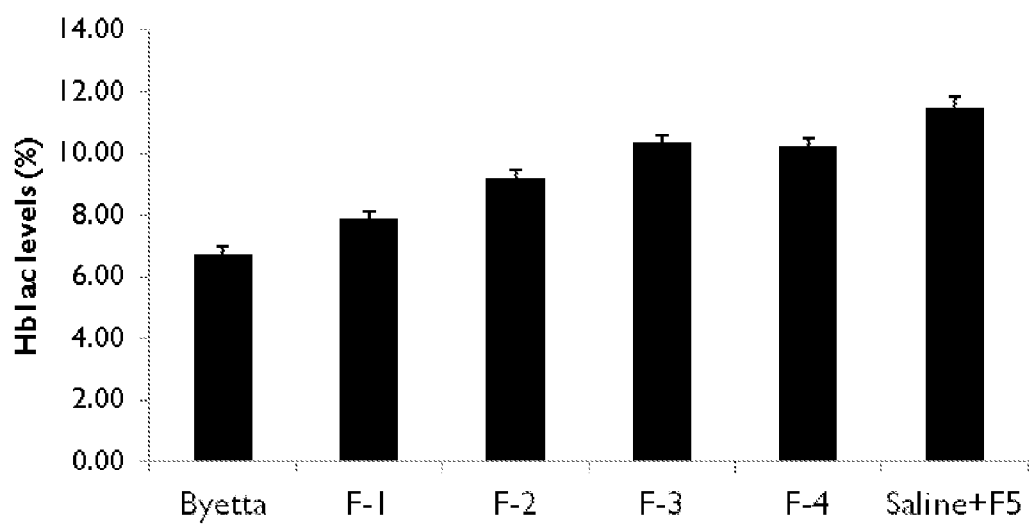
FIG. 7B shows the total mean of glycosylate hemoglobin levels in 10 days treatment.

Collect plasma using EDTA as an anticoagulant. Centrifuge samples for 15 minutes at 1000×g within 30 minutes of collection. Remove plasma and assay immediately or store samples in aliquot at −20° C. or −80° C. Glycosylate hemoglobin levels were measured using a mouse insulin enzyme-linked immunosorbent assay kit (Life Science, Inc, Florida, USA). The glycosylate hemoglobin levels of the different groups at different days are shown in FIG. 7.

Physicochemical Characterization of the NPs and Subsequent MPs

Bovine serum albumin (BSA) is a well-known and abundant protein carrier for oral drug delivery (except peptides and proteins). Its major advantages are biodegradability, biocompatibility, safety, non-antigenicity, well tolerability and availability. Furthermore, incorporation of peptides and proteins in primary NPs is challenging as most of the coating polymers are soluble in water and need to be cross-linked to elicit in-vitro prolonged release of the peptides under sink conditions. In the case of BSA NPs, widely accepted as nanocarriers, the issue is even more complicated. Any denaturation process of albumin, including cross linking with glutaraldehyde, denaturation by heat or use of organic solvents will obviously affect the chemical integrity of the peptide or protein as observed also in the present work.

Figure 8A:
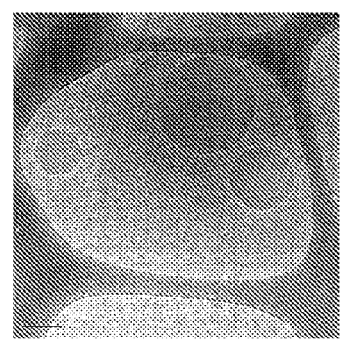
FIGS. 8A-8B present Cryo-TEM images of (FIG. 8A) DX-50 NPs and (FIG. 8B) DX-150 NP formulations.
Figure 8B:
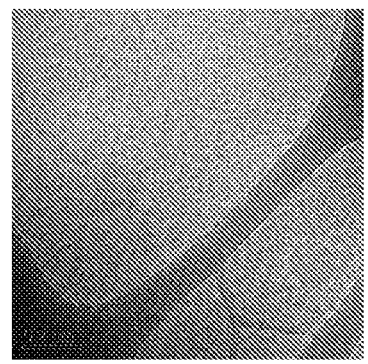

To avoid such a drawback, the BSA matrix was combined with the polysaccharide dextran which can be cross-linked via its reactive hydroxyl groups as shown in FIG. 8 [**Polysaccharides as building blocks for nanotherapeutics]. To achieve a stable nanoparticulate system, the reactive hydroxyl groups of dextran were cross-linked using TSMP, under suitable pH conditions.

Various formulations were prepared by varying different parameters, such as pH, type of cross-linking molecule, TSMP amount, dextran amount. The BSA NPs containing exenatide prepared with glutatraldehyde as cross-linker exhibited a mean diameter size of 59.34±0.32 nm based on triplicate measurement with a poly dispersity index (PDI) value of 0.138 reflecting a narrow size range and a zeta potential value of −50.3±3.03 mV. The properties of the NPs formulations composed of BSA:dextran blend are presented in Table 2. Based on the data depicted in Table 2, two formulations differing in dextran amount: 50 mg and 150 mg were selected as previously mentioned. The mean diameter of the NPs, irrespective of the formulation, ranged from 190 to 210 nm, with a relative narrow distribution range as reflected by the relative low PDI values observed.

Visualization of the primary NPs composed of the BSA/dextran blend was carried out using Cryo TEM (FIG. 1A-B). The images show a spherical morphology of the NPs regardless the difference in composition with a diameter size similar in range value to the range observed with Zetasizer measurements.

Figure 9A:
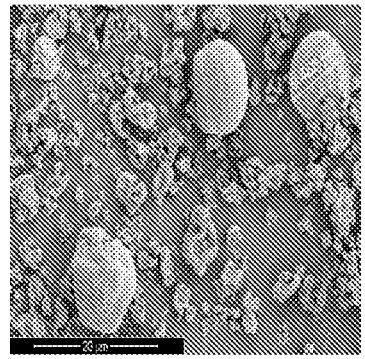
FIGS. 9A-9C show XHR-SEM images of (FIG. 9A) Glut-1 MPs, (FIG. 9B) DX-50 MPs and (FIG. 9C) DX-150 MPs formulations.
Figure 9B:
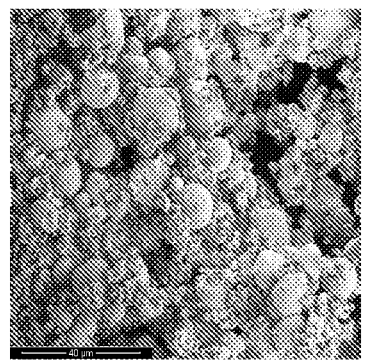
Figure 9C:
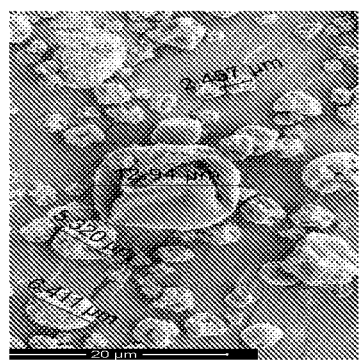

The various NP-loaded MPs characterization was mainly visualized by XHR SEM analysis (FIG. 9A, B, C). The microencapsulated NPs, showed that the coating of the MPs is smooth, ranging qualitatively in size from 1 to 15 µm and the MPs are deflated as a result of the vacuum applied for SEM visualization.

The final exenatide content in Glut-1, DX-50 and DX-150 was 0.147, 0.153 and 0.158% w/w respectively, leading to an encapsulation yield efficiency of approximately 40% irrespective of the formulation.

Rats Pharmacokinetics and Absorption Studies

Figure 10:
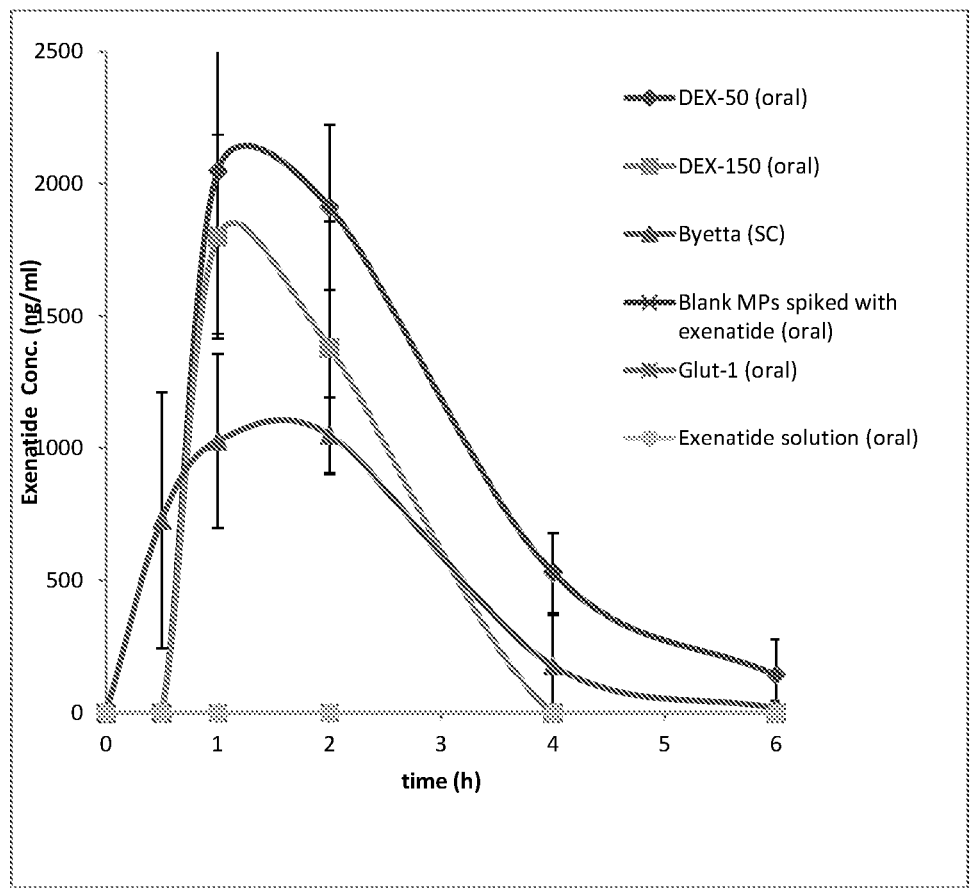
FIG. 10 shows the pharmacokinetic profile of exenatide in rats following subcutaneous injection of Byetta™ and exenatide solution at a dose of 20 µg/rat (56 µg/kg) and oral administration of various formulations at a dose of 50 µg/rat (165 and 65 µg/kg for DEX50 and DEX150 respectively).

Exenatide plasma levels from 3 rats, for each treatment are presented in FIG. 10. At 8 and 24 hours, exenatide plasma concentrations were below the detection limit of the kit irrespective of the formulation, hence data are not shown. Furthermore, it can noted from the results presented in FIG. 10 that the blank MPs formulation (prepared with DX-50 NPs with no exenatide) spiked with exenatide solution, the Glut-1 formulation and the free exenatide solution administered orally did not elicit any detectable exenatide plasma level. It was also observed that the actual exenatide elicited a plasma profile close to the profile of the commercial Byetta™ product whereas the formulation DX-50 elicited a higher pharmacokinetic profile than DX-150 but both were administered at much higher dose that the injectable preparations (165 µg/kg versus 65 µg/kg respectively).

Indeed, following calculations of the pharmacokinetic parameters it can clearly be noted following normalization of the dose that the highest AUC value was elicited by the Byetta injection, followed by the exenatide injected solution, the DX-50 and DX-150 formulation. Furthermore, irrespective of the dose all the formulations elicited $C_{max}$ values higher than 1,000 ng/ml and no difference in the $T_{max}$ values. More importantly, ANOVA analysis pointed out that there is no significant difference between the normalized AUC values between Byeatt and Exenatide solution and the DEX-50 oral suspension. The only significant difference was with DEX10-50 which elicited a relative oral bioavailability of 46.5%.

TABLE 2

Composition and properties of the different NPs formulations prepared from a blend of BSA and Dextran

| Dextran 12 KDa amount (mg) | pH | TSMP (mg) | Mean diameter (nm) | PDI | Zeta Potential (mV) |
|---|---|---|---|---|---|
| 50 | 8.5 | 50 | 192.7 ± 3.5 | 0.370 | −39.5 |
| 50 | 10 | 50 | 91.4 ± 1.3 | 0.429 | −45.7 |
| 50 | 12 | 50 | 38.6 ± 5.5 | 0.699 | −44.7 |
| 50 | 8.5 | 5 | NA | NA | NA |
| 50 | 8.5 | 75 | 504.9 ± 1.8 | 0.399 | −38.9 |
| 50 | 8.5 | 100 | NA | NA | NA |
| 100 | 8.5 | 50 | 337 ± 6 | 0.316 | −41.3 |
| 150 | 8.5 | 50 | 355.4 ± 6.4 | 0.259 | −40.5 |
| 200 | 8.5 | 50 | 691.4 ± 17.3 | 0.364 | −42.65 |
| 50 | 8.5 | 50 | 189.9 ± 2.4 | 0.335 | −40.5 |
| 5 | 8.5 | 50 | NA | NA | NA |
| 5 | 8.5 | 50 | NA | NA | NA |
| 5 | 8.5 | 50 | NA | NA | NA |
| 5 | 8.5 | 50 | NA | NA | NA |

TABLE 3

Average PK parameter values (mean ± SE) following S.C injection of Byetta and exenatide solution (Exe. Sol.) at a dose of 65 µg/kg or oral administration of DX-50 and DX-150 at a dose of 165 µg/kg, N = 3

| Formulation | T ½ (h) | T max (h) | C max (ng/mL) | CL (mL/h/kg) | AUC all (h*ng/mL) | AUC/D | F relative (%) |
|---|---|---|---|---|---|---|---|
| Byetta SC | 0.76 ± 0.09 | 1.33 ± 0.33 | 1216.56 ± 5.91 | 18.70 ± 2.12 | 3101.11 ± 369.67 | 0.16 ± 0.02 | |
| Exe. Sol. SC | 0.21 ± 0.00 | 0.83 ± 0.17 | 1057.29 ± 146.36 | 23.43 ± 4.48 | 2637.10 ± 544.43 | 0.13 ± 0.03 | 85.04 ± 17.56 |
| DX-50 PO | 1.64 ± 0.13 | 1.33 ± 0.33 | 2089.53 ± 324.45 | 27.25 ± 1.72 | 5944.55 ± 394.88 | 0.12 ± 0.01 | 76.68 ± 5.10 |
| DX-150 PO | 0.23 ± 0.00 | 1.00 ± 0.00 | 1800.65 ± 222.27 | 48.50 ± 6.90 | 3599.25 ± 575.02 | 0.07 ± 0.01 | 46.43 ± 7.42 |

Observations

All the procedures related to animal handling, care, and the treatment in this study were performed according to the guidelines approved by the Institutional Animal Care and Use Committee (IACUC) following the guidance of the Association for Assessment and Accreditation of Laboratory Animal Care (AAALAC).

All values in the figures and text are expressed as mean standard error (s.e.m.) of the mean of n observations. For the in vivo studies, n represents the number of animals studied. In the experiments involving histology the figures shown are representative at least three experiments (histological coloration) performed on different experimental days on the tissues section collected from all the animals in each group. Data sets were examined by one- or two-way analysis of variance, and individual group means were then compared with Student's unpaired t test. A p-value less than 0.05 was considered significant.

Discussion

The therapeutic efficacy and safety of different formulations of Exenatide (F1-F5) was evaluated in OB/OB mice. In particular, there were no significant differences in body weight after administration of Exenatide (F1-F5) and Byetta (FIG. 3).

In the preliminary experiments with Byetta, after 1 h of glucose injection, mice were administered with Byetta, as shown in FIG. 4; a reduction in blood glucose levels is demonstrated until 6 h. This result supports the idea that Byetta represent a goal standard in the treatment of diabetes. In addition, different formulations of Exenatide (F1-F4) were compared with Byetta treatment. It is of note that the Exenatide formulations (F1-F4) were orally administered, while the Byetta composition was administered by injection. The results showed that, daily oral administration of F-1 and F-2 are able to reduce the increase of blood glucose levels in OB/OB mice (FIG. 5). On this basis, it is speculated that these two formulations show the most interesting results.

The data in FIG. 6 demonstrates the plasma insulin levels of the different groups at different days. As can be observed, the treatment with the different formulations of Exenatide (F1-F5) is able to increase the insulin levels as well as treatment with Byetta.

Moreover, during the 10 days treatment, it was found that Byetta injection reduces the levels of glycosylated hemoglobin (HbA1c) in OB/OB mice (FIGS. 7-11). The rate of glycosylated hemoglobin clarified, as compared to FIG. 5, shows that only two formulations of Exenatide F-1 and F-2 show an effect in the reduction of glycosylated hemoglobin levels.

From this it was concluded that daily oral administration of Exenatide F-1 (and to a much lesser extent oral administration of F-2, because the peptide is cross-linked by glutaraldehyde and loss part of its activity), may have a beneficial effect in the symptomatic treatment of diabetes.

Double Nanoencapsulation of h-Insulin

Double nanoencapsulated samples comprising h-insulin were prepared for obtaining an injectable dry powder, for eliciting prolonged release of the peptide in vivo.

h-Insulin Primary Nanoencapsulation with HSA:

200 mg of human serum albumin (HSA) were dissolved in 5 ml of DDW under stirring. Separately, 20 mg of human or bovine insulin were dissolved in 5 ml of DDW and vortexed for 30 seconds. The h-insulin solution was then added to the HSA solution and stirred for 30 minutes to complete peptide dissolution. The pH of the resulted solution was adjusted to 7.4-8 with NaOH 0.1M. Then, 20 ml of acetone were injected quickly (within 20 seconds) under vigorous stirring (900 rpm) to elicit formation of HSA nanocapsules load with h-insulin (solution A). Solution A was covered with aluminum foil to avoid acetone evaporation and was stirred over 1 hour at 900 rpm. Samples (50-100 µl) were withdrawn following one hour stirring for Zeta potential and size measurements. Separately, a solution of PLGA 100K (50:50) was dissolved in 80 ml of acetonitrile and added to solution A.

Nanoencapsulation of HSA/h-Insulin Nanoparticles into by PLGA Using Nanospray Dryer—Organic Mode Nanocapsules were prepared via spray drying on the NSD B-90 operating at 'closed loop' mode, hence, $N_2$ (g) and $CO_2$ (g) were flowed in the system instead of air. In all experiments, gas flow was about 120 l/min. The air was soaked with volatile vapors and humidity transferred to a Dehumidifier unit for drying and condensation, then was returned dry to the system in a circular path. Spray drying was carried out at low temperatures ($T_m$=30°-60° C.) with mesh size membrane 4 µm. Various formulations of different HSA/h-insulin/PLGA ratios were prepared. Unlike conventional spray dryers that operate on turbulent flow, the NSD B-90 operates on a laminar flow; hence gentle heating is achievable, thus making the system compatible for heat-sensitive biopharmaceutical products.

Physicochemical Characterization of Drug-Loaded Primary Nanocapsules

Insulin Content within the Primary Nanocapsules

An appropriate analytical method by HPLC was developed at the following conditions:

A c4 column was used for separation and analyzing h-insulin (RESTEK viva 4.6 mm×250 mm, i.d., 5 µm particles, Bellefonte, Pa. USA). Column temperature was kept at 45° C. Mobile phase A was acetonitrile (ACN), and mobile phase B was potassium di-hydrogen phosphate ($KH_2PO_4$, 20 mmol/L) adjusted to pH 2.5 with phosphoric acid. The mobile phase was filtered through a 0.45 µm membrane filter and degassed via vacuum prior to use.

The following gradient conditions were used for h-insulin: from 30% to 45% mobile phase A in 15 min, and re-equilibrated back to 30% mobile phase A for 3 min. Flow rate was 1.5 mL/min. Injection volume was 20 UV signal was detected at 215 nm.

TABLE 4 h-insulin content in various formulations

| Formulation | Nanoparticles method | Encapsulation efficiency (%) | Content (Insulin/mg formulation) |
|---|---|---|---|
| DEHI-002 | PLGA 100K (3X), insulin (3X) nanoencapsulation | 69 | 15.01 |
| DEHI-003 | PLGA 100K (3X), insulin (1X) nanoencapsulation | 145 | 12.36 |
| DEHI-004 | PLGA 100K (1X), insulin (1X) nanoencapsulation | 25 | 13.09 |

TABLE 5

The zeta potential and particle size of the primary nanocapsules of various formulations

| Formulation | Nanoparticles method | Size (nm) | PDI | Zeta potential (mV) |
|---|---|---|---|---|
| DEHI-002 | PLGA 100K (3X), insulin (3X) double nanoencapsulation | 151.1 | 0.17 | −59.6 |
| DEHI-003 | PLGA 100K (3X), insulin (1X) nanoencapsulation | 150.1 | 0.17 | −61.9 |
| DEHI-004 | PLGA 100K (1X), insulin (1X) nanoencapsulation | 160.9 | 0.10 | |

Freeze-Fractured SEM Images of Nanocapsules at Fluid Interfaces

Figure 11A:
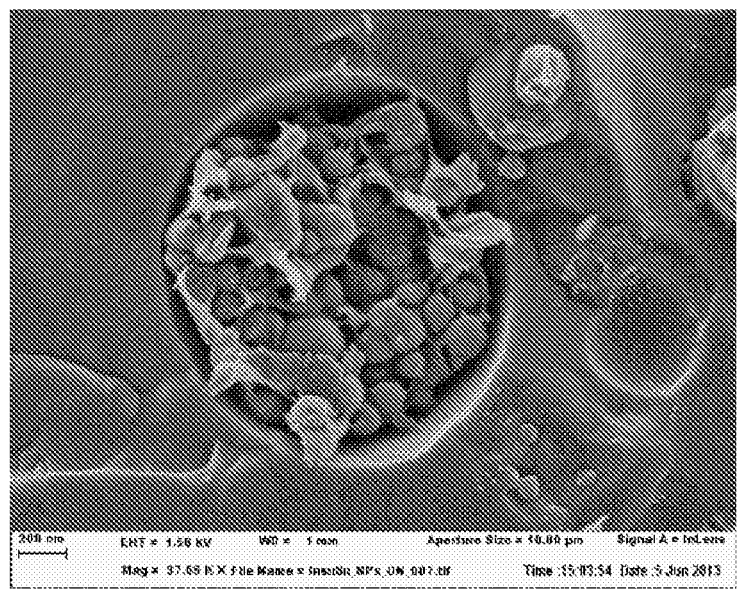
FIGS. 11A-11C are freeze-fractured SEM images of double encapsulated BSA/insulin NPs following a cryo-protection process.
Figure 11B:
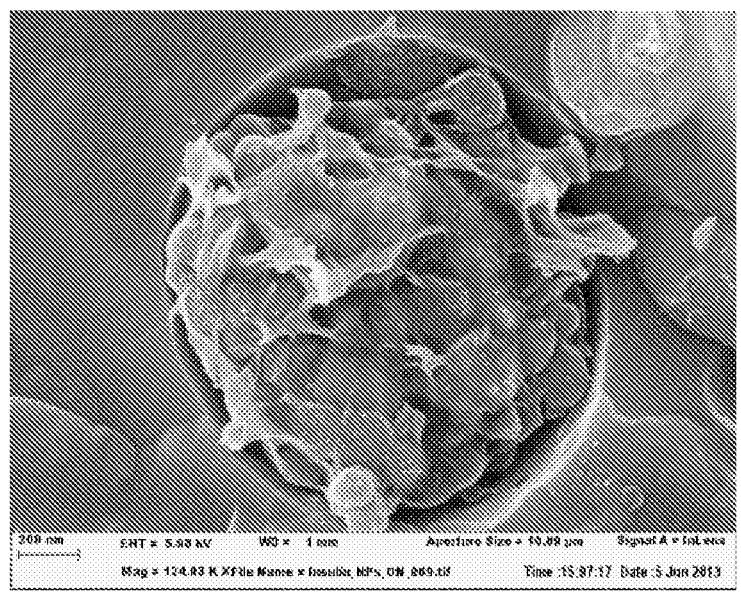
Figure 11C:
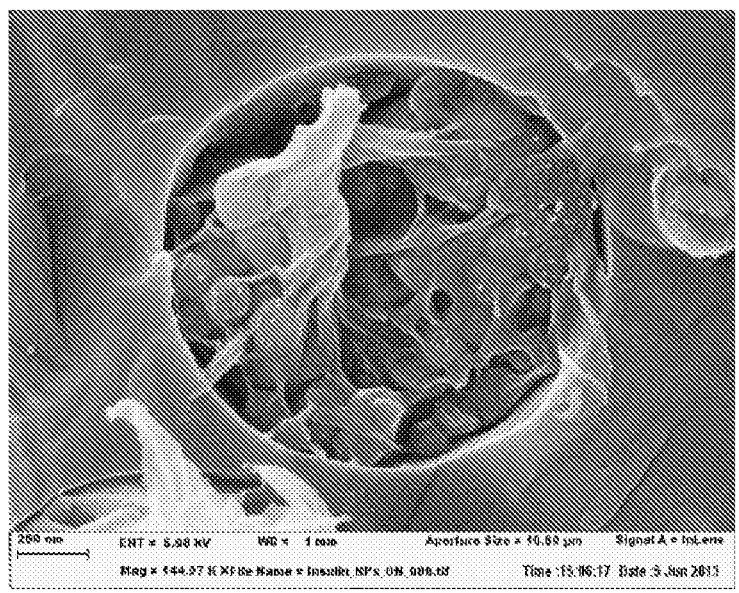

Samples were suspended in ultra pure water+vortex, and then were shaken for at least 30 minutes, prior to freezing. A suspension volume of 1.5 µm was sandwiched between two flat aluminum platelets with a 200 mesh TEM grid used as a spacer between them. The sample was then high-pressure frozen in a HPM010 high-pressure freezing machine (Bal-Tec, Liechtenstein). The frozen samples were mounted on a holder and transferred to a BAF 60 freeze fracture device (Bal-Tec) using a VCT 100 Vacuum Cryo Transfer device (Bal-Tec). After fracturing at a temperature of −120° C. samples were etched at −110° C. for 5 minutes and coated with 3 nm Pt/C by double axis rotary shadowing. Samples were transferred to an Ultra 55 SEM (Zeiss, Germany) using a VCT 100 and were observed using a secondary electrons in-lens detector at 1.5 kV at a temperature of −120° C. The SEM images are shown in FIGS. 11A-11C.

Induction of Diabetes Mellitus (DM)

The DM was induced in the rats by intravenous injection of streptozotocin (STZ) diluted in 0.05M citrate buffer (50 mg/kg body weight). Two weeks afterwards, animals selected as diabetic were those that exhibited fasting glycemia above 250 mg/dL. Glycemia was measured by the glucose oxidase method (Bergmeyer and Bernt, 1974) using a clinical glucometer (Contour™, BAYER).

The diabetic rats were then used to evaluate the hypoglycemic effects of different formulations containing insulin nanocapsules via oral feeding at 5; 10 IU/(175; 350 µg) and subcutaneous injection at 5 IU (175 µg) per animal in different conditions (fasted and non fasted).

Figure 12:
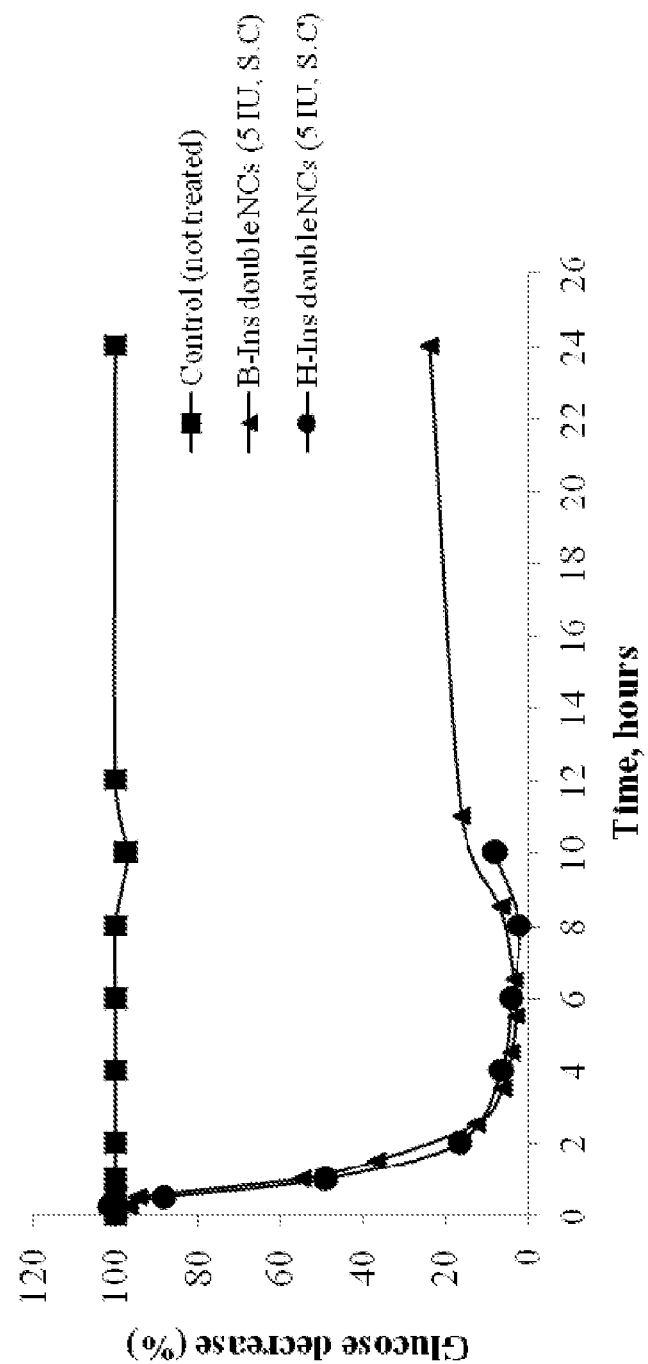
FIG. 12 shows the blood glucose levels following subcutaneous administration of the various insulin loaded nanoparticles formulations in fasting conditions (N=3).
Figure 13:
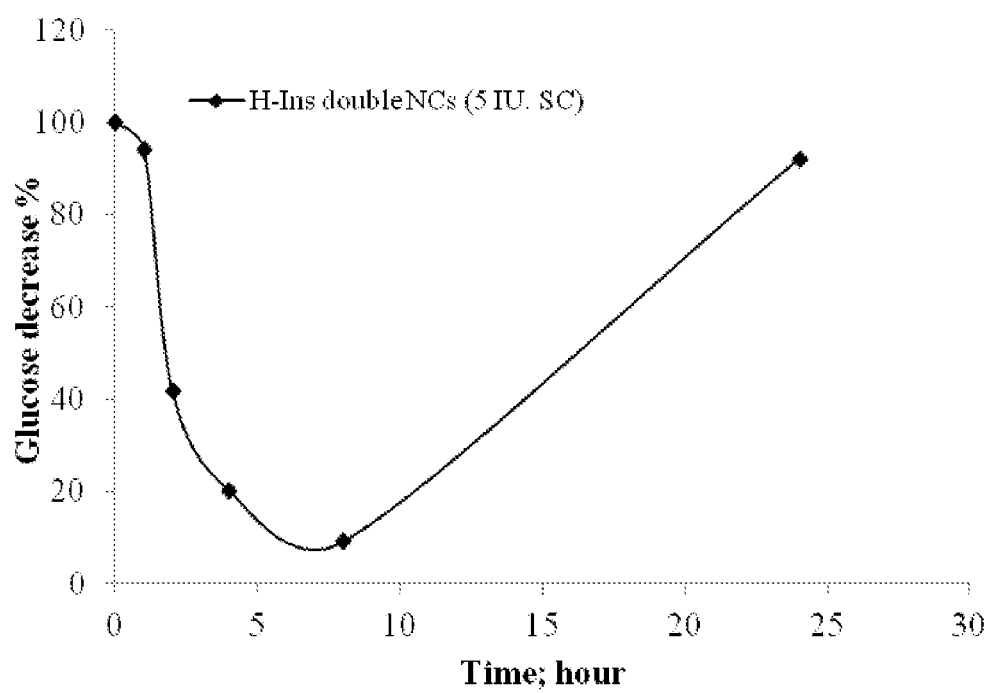
FIG. 13 shows blood glucose levels following subcutaneous administration of h-insulin loaded nanoparticles formulation in non-fasting conditions (N=3).

FIGS. 12-13 show the blood glucose levels following subcutaneous administration of the various insulin loaded nanoparticles formulations in fasting and non-fasting conditions (N=3), respectively.

It can be seen from the SEM images that primary HSA nanocapsules of h-insulin are nanoencapsulated in larger nanocapsules of PLGA. These primary nanocapsules are also coated internally by the polymer PLA suggesting that the insulin release may be controlled upon i.m. or s.c. injection. This assumption was verified (as can be seen in FIGS. 12-13), as the injection of both types of insulin in double nanocapsules elicit a marked prolonged decrease in blood glucose over 24 h in fasting conditions, whereas in non fasting conditions the effect is shorter. It can be concluded that the novel technique does not affect at least markedly the pharmacological activity of the insulin.

The invention claimed is:

1. A nanoparticle comprising a matrix of albumin and a glucan, the matrix encapsulating a hydrophilic active agent, the glucan being at least partially cross-linked by sodium trimetaphosphate (STMP),
wherein the albumin, at least one glucan and at least one hydrophilic active agent are uniformly distributed.

2. The nanoparticle of claim 1, wherein said albumin is selected from human serum albumin (HSA) and bovine serum albumin (BSA).

3. The nanoparticle of claim 1, wherein the glucan is an α-glucan.

4. The nanoparticle of claim 3, wherein said a-glucan is selected from dextran, glycogen, pullulan, starch, lichenin, mannan, galactomannan, arabinoxylan, and galacton.

5. The nanoparticle of claim 1, wherein said glucan has a molecular weight of between about 5 KDa and 2,000 KDa.

6. The nanoparticle of claim 1, wherein said hydrophilic active agent comprises —$NH_2$ moieties.

7. The nanoparticle of claim 1, wherein said hydrophilic active agent is selected from a vitamin, a protein, an anti-oxidant, a peptide, a polypeptide, a carbohydrate, a hormone, an antibody, a monoclonal antibody, a vaccine, a prophylactic agent, a diagnostic agent, a contrasting agent, a nucleic acid, a nutraceutical agent, a small molecule of a molecular weight of less than about 1,000 Da, an electrolyte, a drug, an immunological agent, and combinations thereof.

8. The nanoparticle of claim 7, wherein said hydrophilic active agent is selected from the group consisting of insulin, exenatide, growth hormone, octreotide acetate, lanreotide acetate, goserelin acetate, copaxone, etanercept, and monoclonal antibodies.

9. The nanoparticle of claim 7, wherein said hydrophilic active agent is selected from insulin and exenatide.

10. The nanoparticle of claim 1, having a diameter of at most 500 nm.

11. The nanoparticle of claim 10, having a diameter between about 50 nm and 250 nm.

12. The nanoparticle of claim 1, being a nanosphere or a nanocapsule.

13. A carrier comprising a hydrophobic polymer and a plurality of nanoparticles as claimed in claim 1, the plurality of nanoparticles being (i) encapsulated by said hydrophobic polymer or (ii) embedded in a matrix formed of said hydrophobic polymer.

14. The carrier of claim 13, wherein said hydrophobic polymer is selected from poly(lactic glycolic) acid (PLGA), polymethyl-methacrylate (PMMA), hydroxypropyl methylcellulose (HPMC), poly(lactic acid) (PLA), poly(lacto-co-glycolide) (PLG), poly(lactide), polyglycolic acid (PGA), and poly(hydroxybutyrate).

15. The carrier of claim 13, wherein the nanoparticles are encapsulated in microcapsules or embedded in microparticles, the microcapsules or microparticles having a diameter of between 1 and 30 microns.

16. A pharmaceutical composition comprising the nanoparticle of claim 1 and further comprising a carrier.

17. The pharmaceutical composition of claim 16, being adapted for topical, oral, inhalation, nasal, transdermal, ocular or parenteral administration of said hydrophilic active agent.

18. The delivery system of claim 13, further encapsulated within a biodegradable capsule, wherein said biodegradable capsule is optionally in the form of an entero-coated capsule.

19. A process for the preparation of a nanoparticle comprising albumin, a glucan and a hydrophilic active agent, the glucan being at least partially cross-linked by sodium trimetaphosphate (STMP), the process comprising:
  mixing a first aqueous solution comprising albumin and said glucan with a second aqueous solution comprising said hydrophilic active agent to form a mixture;
  delivering an organic solvent into said mixture; and
  adding sodium trimetaphosphate to said mixture to thereby at least partially cross-link said glucan for obtaining said nanoparticle.

* * * * *